United States Patent [19]

Brewster et al.

[11] Patent Number: 5,401,849
[45] Date of Patent: * Mar. 28, 1995

[54] 4-PYRIDYL-1,3-DIOXANE DERIVATIVES

[75] Inventors: Andrew G. Brewster, Macclesfield; George R. Brown, Wilmslow; Alan W. Faull, Macclesfield; Reginald Jessup, Sandbach; Michael J. Smithers, Macclesfield, all of England

[73] Assignee: Zeneca Limited, London, England

[*] Notice: The portion of the term of this patent subsequent to Oct. 1, 2008 has been disclaimed.

[21] Appl. No.: 78,658

[22] Filed: Jun. 21, 1993

Related U.S. Application Data

[62] Division of Ser. No. 951,760, Sep. 25, 1992, Pat. No. 5,248,780, which is a division of Ser. No. 310,235, Feb. 14, 1989, Pat. No. 5,166,213.

[30] Foreign Application Priority Data

Feb. 16, 1988 [GB] United Kingdom ............... 8803516
Oct. 21, 1988 [GB] United Kingdom ............... 8824666

[51] Int. Cl.$^6$ .......................................... C07D 405/04
[52] U.S. Cl. .................................................. 546/268
[58] Field of Search ............... 546/268, 256; 514/333, 514/336

[56] References Cited

U.S. PATENT DOCUMENTS

| | | | |
|---|---|---|---|
| 4,554,011 | 11/1985 | Loh | 71/88 |
| 4,567,197 | 1/1986 | Brewster et al. | 514/452 |
| 4,668,698 | 5/1987 | Brewster et al. | 514/452 |
| 4,704,399 | 11/1987 | Main | 514/452 |
| 4,723,037 | 2/1988 | Harris | 562/470 |
| 4,735,963 | 4/1988 | Matassa et al. | 514/433 |
| 4,736,057 | 5/1988 | Guildford et al. | 560/59 |
| 4,745,198 | 5/1988 | Brewster et al. | 549/369 |
| 4,772,625 | 9/1988 | Brewster | 514/452 |
| 4,775,684 | 10/1988 | Smithers | 514/452 |
| 4,775,685 | 10/1988 | Brewster | 514/452 |
| 4,803,220 | 2/1989 | Brewster et al. | 514/452 |
| 4,806,563 | 2/1989 | Smithers | 514/452 |
| 4,822,815 | 4/1989 | Brown et al. | 514/444 |
| 4,824,858 | 4/1989 | Brown et al. | 514/336 |
| 4,831,046 | 5/1989 | Brown et al. | 514/381 |
| 4,845,120 | 7/1989 | Brown et al. | 514/452 |
| 4,895,962 | 1/1990 | Brewster | 549/373 |
| 4,895,963 | 1/1990 | Brewster | 549/375 |
| 4,900,846 | 2/1990 | Harris | 549/373 |
| 4,902,712 | 2/1990 | Smithers | 514/452 |
| 4,908,380 | 3/1990 | Brewster et al. | 514/452 |
| 4,921,866 | 5/1990 | Brewster et al. | 514/336 |
| 4,921,979 | 5/1990 | Smithers | 549/375 |
| 4,925,869 | 5/1990 | Smithers | 514/452 |
| 5,047,412 | 9/1991 | Brown et al. | 514/307 |
| 5,053,415 | 10/1991 | Brewster et al. | 514/336 |
| 5,072,008 | 12/1991 | Harris | 549/475 |
| 5,126,368 | 6/1992 | Smithers | 514/452 |
| 5,166,377 | 11/1992 | Brewster et al. | 554/43 |
| 5,169,974 | 12/1992 | Harris et al. | 558/414 |
| 5,219,874 | 6/1993 | Faull et al. | 514/365 |

FOREIGN PATENT DOCUMENTS 201352 11/1986 European Pat. Off. .

OTHER PUBLICATIONS

C. W. Thornber; Isoterism and Molecular Modification in Drug Design (1979).

Primary Examiner—Raymond J. Henley, III
Assistant Examiner—Phyllis G. Spivack
Attorney, Agent, or Firm—Cushman Darby & Cushman

[57] ABSTRACT

The invention concerns pharmaceutically useful 1,3-dioxane alkenoic acid derivatives of formula VII and formula XI containing a pyridyl moiety at position 4 of the dioxane ring and in which the groups at positions 2, 4 and 5 have cis-relative stereochemistry, wherein X is hydrogen, alkoxy or hydroxy, Y is vinylene, n is 1 or 2, $A^1$ is alkylene, $R^1$ is a variety of substituents defined hereinafter, Ra and Rb are independently methyl or ethyl, $R^2$ is hydroxy, a physiologically acceptable alcohol residue or alkanesulphonamido, and the pharmaceutically acceptable salts thereof.

3 Claims, No Drawings

4-PYRIDYL-1,3-DIOXANE DERIVATIVES

This is a division of application Ser. No. 07/951,760, filed Sep. 25, 1992, now U.S. Pat. No. 5,248,780, which is a division of 07/310,235, filed Feb. 14, 1989, now U.S. Pat. No. 5,166,213.

PYRIDINE DERIVATIVES

This invention concerns novel pyridine containing heterocyclic compounds and, more particularly, it concerns novel 1,3-dioxan-5-yl alkenoic acids containing a pyridyl moiety attached at position 4 of the 1,3-dioxane ring. The acids of the invention have valuable pharmaceutical properties and the invention includes pharmaceutical compositions containing the novel acids and processes for the manufacture and medical use of the novel acids. Also included in the invention is the use of a novel acid in the production of a medicament for use in treating warm blooded animals such as humans.

It is known that the arachidonic acid metabolite thromboxane $A_2$ (hereinafter referred to as "$TXA_2$") is a powerful vasoconstrictor and a potent aggregator of blood platelets. $TXA_2$ is also a potent constrictor of bronchial and tracheal smooth muscle. $TXA_2$ may therefore be involved in a variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance.

It is believed that $TXA_2$ exerts its physiological action through the thromboxane receptor, at which receptor various other prostanoid contractile substances derived from arachidonic acid, such as prostaglandins $H_2$, $F_2$ alpha and prostaglandin $D_2$, can exert contractile effects. There are two principal ways in which the effects of $TXA_2$ can be ameliorated. The first is by administering a pharmacological agent which preferentially occupies the thromboxane receptor, but yet does not produce the contractile effects which follow the binding of $TXA_2$ (or of prostaglandins $H_2$, $F_2$ alpha and/or $D_2$). Such an agent is said to possess $TXA_2$ antagonist properties. The second way is to administer a pharmacological agent which inhibits one or more of the enzymes involved in the production of $TXA_2$ and in particular which inhibits the enzyme known as thromboxane synthase ($TXA_2$ synthase). Such an agent is said to be a $TXA_2$ synthase inhibitor. Accordingly, it may be seen that agents which possess $TXA_2$ antagonist properties and which inhibit $TXA_2$ synthase may be expected to be of therapeutic value in the treatment of one or more of the above mentioned diseases or other diseases in which $TXA_2$ is involved. Also, agents which possess $TXA_2$ antagonist properties may be expected to be of value additionally in treating those diseases in which prostaglandins $H_2, F_2$ alpha and/or $D_2$ are involved, for example especially in asthmatic and inflammatory diseases. Although 1,3-dioxane $TXA_2$ antagonists are known (for example, in European patent, publication number 94239B1), as are certain $TXA_2$ synthase inhibitors (for example, in European patent application, publication number 98690A2), obtaining compounds which combine both properties to a useful extent is not straightforward.

However, we have now discovered (and this is the basis for our invention) that certain 1,3-dioxan-5-yl alkenoic acids of the formula I (set out, together with the other chemical structures, at the end of this specification) containing a pyridyl moiety attached to position 4 of the 1,3-dioxane ring surprisingly are good inhibitors of $TXA_2$ synthase and also possess significant $TXA_2$ antagonist properties and are useful pharmaceutical agents.

According to the invention there is provided a 1,3-dioxane alkenoic acid derivative of the formula I (set out hereinafter together with the other chemical formulae in Roman numerals) wherein: $A^1$ is (1–6C)alkylene; $R^1$ is (1–6C)alkyl, trifluoromethyl, (3–6C)cycloalkyl or (1–4C)alkoxy(1–4C)alkyl, or is a group of the formula $R^3.A^2$- in which $R^3$ is pyridyl, phenyl or phenyl bearing 1 or 2 substituents selected from halogeno, trifluoromethyl, nitro and cyano, and in which $A^2$ is (1–6C)alkylene, oxy(1–6C)alkylene, (2–6C)alkenylene or a direct bond to $R^3$; $R^2$ is hydroxy, a physiologically acceptable alcohol residue, or (1–4C)alkanesuphonamido; X is hydrogen, hydroxy or (1–4C)alkoxy; Y is vinylene; and n is the integer 1 or 2; or a pharmaceutically acceptable salt thereof.

It will be appreciated that the compounds of formula I possess asymmetric carbon atoms and may exist and be isolated in racemic and optically active forms. The invention includes both the racemic forms and any optically active form (or mixtures thereof) which is capable of antagonising one or more of the actions of $TXA_2$ and inhibiting the synthesis of $TXA_2$, it being well known in the art how to prepare individual optical isomers (for example by synthesis from optically active starting materials or resolution of a racemic form) and how to determine the $TXA_2$ antagonist properties and $TXA_2$ synthase inhibitory properties using one or more of the standard tests referred to hereinafter.

It will be understood that the groups at positions 2, 4 and 5 of the 1,3-dioxane moiety of formula I have cis-relative stereochemistry, as have the groups adjacent to the vinylene group Y (i.e. the latter compounds exist as the "Z" isomer). Further, although a particular configuration is shown in the chemical formulae attached hereto, this does not necessarily correspond to the absolute configuration.

It is also to be understood that the generic term "alkylene" includes both straight chain and branched chain alkylene groups such as ethylene and ethylidene and other generic terms are to be construed similarly. However, when a specific term such as "butyl" is used, it is specific to the straight chain or "normal" butyl group, branched chain isomers such as "t-butyl" being referred to specifically when required.

Particular values for $R^1$ when it is (1–6C)alkyl include, for example, methyl, ethyl, isopropyl and t-butyl, of which the latter two are preferred; when it is (3–6C)cycloalkyl include, for example, cyclopentyl and cyclohexyl; and when it is (1–4C)alkoxy(1–4C)alkyl include, for example, 1,1-dimethyl-2-methoxyethyl and 1-methyl-1-propoxyethyl.

Particular values for $R^2$ when it is a physiologically acceptable alcohol residue are those which render the subsequent ester biodegradable and are chosen from, for example, (1–6C)alkyl optionally bearing a hydroxy or (1–4C)alkoxy substituent, such as methyl, ethyl, 2-hydroxyethyl, 2-methoxyethyl, propyl or 3-hydroxypropyl; phenyl; and benzyl; the latter two of which may optionally bear 1 or 2 optional substituents selected from halogeno (such as fluoro, chloro, bromo or iodo), (1–4C)alkyl (such as methyl or ethyl) and (1–4C)alkoxy (such as methoxy or ethoxy).

Particular values for $R^2$ when it is (1–4C)alkanesulphonamido include, for example, methanesulphonamido, ethanesulphonamido and butanesulphonamido.

Particular values for $A^1$ when it is (1–6C)alkylene include, for example: methylene, ethylene, trimethylene, tetramethylene, 1,1-dimethylethylene and 1,1-dimethyltrimethylene.

Particular values for $A^2$ when it is (1–6C)alkylene include, for example, (1–4C)alkylene (such as methylene, ethylene, trimethylene, isopropylidene and 1,1-dimethylethylene) and 3,3-pentylidine; when it is (2–6C)alkenylene include, for example, vinylene, 1,3-propenylene and 1,4-buten-2-ylene; and when it is oxy(1–6C)alkylene include, for example, oxymethylene, oxytetramethylene (i.e. a group of the formula: —O.(CH$_2$)$_4$—), 1-oxy-1-methylethyl (i.e. a group of the formula: —O.C(CH$_3$)$_2$—) and 2-oxy-1,1-dimethylethyl (i.e. a group of the formula —O.CH$_2$.C(CH$_3$)$_2$—), it being understood that the oxy link is to the group $R^3$ and not the 1,3-dioxane ring.

A particular value for $R^3$ when it is pyridyl is, for example, 3-pyridyl.

A particular value for an optional halogeno substituent when $R^3$ is halogenophenyl is, for example, fluoro, chloro or bromo.

A particular value for X when it is (1–4C)alkoxy, is for example, methoxy or ethoxy. A preferred value for X is, for example, hydrogen.

By way of example, a generally preferred value for n is 1, for Y is cis-vinylene and for $A^1$ is ethylene or trimethylene.

A group of compounds of the invention of particular interest comprises compounds of formula II wherein: $A^3$ is (1–4C)alkylene; $R^4$ is trifluoromethyl, branched (3–6C)alkyl, or is a group of the formula $R^5.A^4$- in which $R^5$ is pyridyl, phenyl or phenyl bearing 1 or 2 substituents selected from halogeno, trifluoromethyl, nitro and cyano, and in which $A^4$ is (1–4C)alkylene, oxy(1–4C)alkylene or a direct bond to $R^5$; Y is vinylene; Q is a 3-pyridyl or 4-pyridyl moiety; and X, $R^2$ and n have any of the meanings defined above; together with the pharmaceutically acceptable salts thereof when $R^2$ is hydroxy or (1–4C)alkanesulphonamido.

In the above group, a preferred value for Y is cis-vinylene, for $R^2$ is hydroxy, for n is the integer 1 and for X is hydrogen.

A further group of compounds of the invention of particular interest comprises compounds of formula III wherein A3 is (1–4C)alkylene; $R^5$ is pyridyl, phenyl or phenyl bearing 1 or 2 substituents selected from halogeno, trifluoromethyl, nitro and cyano; and $A^4$ is (1–4C)alkylene, oxy(1–4C)alkylene or a direct bond to $R^5$; together with the pharmaceutically acceptable salts thereof.

Particular values for $A^3$ include, for example, those defined above for $A^1$ when it is (1–4C)alkylene, for example, ethylene, trimethylene and 1,1-dimethylethylene, of which values, ethylene is generally preferred.

Particular values for $A^4$ include, for example, those defined above for $A^2$ when it is a direct bond, (1–4C)alkylene or oxy(1–4C)alkylene, such as a direct bond, isopropylidene, 1,1-dimethylethylene and 1-oxy-1-methylethyl (i.e. a group of the formula: —O.C(CH$_3$)$_2$—); and for $R^5$ include, for example, 3-pyridyl, phenyl, 4-halogenophenyl (such as 4-chloro- or 4-bromophenyl), 2-halogenophenyl (such as 2-fluoro- or 2-chloro-phenyl), dihalogenophenyl (such as 3,4-difluoro-, 3,4-dichloro- or 2,4-dichloro-phenyl), nitrophenyl (such as 2-nitro-, 3-nitro or 4-nitro-phenyl), 2-cyanophenyl, 4-cyanophenyl, 2-trifluoromethylphenyl and 4-trifluoromethylphenyl.

Specific values for $R^1$ include, by way of example: trifluoromethyl, isopropyl, t-butyl, cyclohexyl, phenyl, 2-chlorophenyl, 3-chlorophenyl, 2-cyanophenyl, 4-cyanophenyl, 4-nitrophenyl, 2-chloro-5-nitrophenyl, 3,4-dichlorophenyl, 2,4-dichlorophenyl, 2-trifluoromethylphenyl, 4-trifluoromethylphenyl, 1-phenoxy-1-methylethyl (in which the phenoxy moiety may optionally bear 2-fluoro, 2-nitro, 2-trifluoromethyl, 3-fluoro, 3-bromo, 3-nitro, 4-fluoro, 4-bromo, 4-cyano, 4-nitro, 2,4-dichloro, 3,4-difluoro or 3,4-dichloro substituents), 3-pyridyl, 4-pyridyl, 1-methyl-1-(3-pyridyloxy)ethyl, 1-propoxy-1-methylethyl and 1,1-dimethyl-2-phenylethyl (in which the phenyl moiety may optionally bear 3-bromo, 3-nitro, 4-fluoro, 4-nitro, 4-trifluoromethyl, 3,4-difluoro or 3,4-dichloro substituents), styryl and 2-nitrostyryl.

In the above compounds of the invention, a particularly preferred value for $R^2$ is, for example, hydroxy and for X is, for example, hydrogen.

Particular novel compounds of the invention are described in the accompanying Examples and are provided, together with their pharmaceutically acceptable salts, as a further feature of the invention. The compounds of Examples 4, 8, 11 and 28 are particularly preferred.

Although all of the formula I compounds can form salts with suitable acids, it will be appreciated that the compounds of formula I are amphoteric when R2 is hydroxy or alkanesulphonamido and can form salts with acids as well as bases. Particular pharmaceutically acceptable salts for such compounds therefore include, for example, alkali metal and alkaline earth metal salts, ammonium salts, salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide, as well as salts with acids affording physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be manufactured by conventional procedures of organic chemistry well known in the art for the manufacture of structurally analogous compounds. Such procedures are provided as a further feature of the invention and are illustrated by the following representative procedures in which $R^1$, $R^2$, X, Y, $A^1$ and n have any of the meanings defined hereinbefore.

(a) For those compounds of formula I in which $R^2$ is hydroxy, an aldehyde of the formula IV is reacted with a Wittig reagent of the formula: $R_3P=CH.A^1.CO_2^- M^+$ wherein R is (1–6C)alkyl or aryl (especially phenyl, which is preferred) and $M^+$ is a suitable metal cation, for example an alkali metal cation such as the lithium, sodium or potassium cation.

The process in general produces the required compounds of formula I in which the substituents adjacent to the vinylene group Y have predominantly the preferred cis-relative stereochemistry i.e. in the "Z" isomeric form. However the process also produces generally small amounts of the analogous compounds having trans-relative stereochemistry (ie. the "E" isomeric form) which may be removed by a conventional procedure, such as chromatography or crystallisation.

The process may be conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, −80° C. to 40° C. but is conveniently carried out at or near room temperature, for example in the range 0° to 35° C.

(b) For those compounds wherein X is hydroxy, a compound of the formula V wherein P is a protected hydroxy group, is deprotected by conventional means.

Examples of particularly suitable protected hydroxy groups include, for example, (1-4C)alkoxy (such as methoxy), benzyloxy, allyloxy, tetrahydropyran-2-yloxy, (1-4C)alkanesulphonyloxy (especially methanesulphonyloxy) and trialkylsilyloxy of up to 10 carbon atoms.

The deprotection conditions used will necessarily depend on the nature of the protected hydroxy groups. The removal of specific hydroxyl protecting groups is well documented in standard organic chemistry books and such conventional procedures well known in the art are included within the processes of the invention. Thus, for example, specific groups may be removed as follows: (1), allyl or tetrahydropyran-2-yl: by treatment with strong acid such as trifluoroacetic acid, at e.g 10° to 40° C. (2) trialkylsilyl (such as t-butyldimethylsilyl, which is preferred): by reaction with aqueous tetrabutylammonium fluoride or sodium fluoride conveniently in a suitable solvent or diluent, such as tetrahydrofuran, or t-butyl methyl ether, and generally at or near ambient temperature, e.g. in the range 10° to 35° C.; (3) alkanesulphonyl: by hydrolysis in the presence of a base (such as sodium or potassium hydroxide) in a suitable aqueous solvent [such as an aqueous (1-4C)alkanol] and at e.g. 0° to 60° C.; (4) alkyl: by treatment with an alkali metal thioalkoxide or diphenylphosphide (such as sodium thioethoxide in a solvent such as N,N-dimethylformamide at e.g 50°-160° C. or lithium diphenylphosphide in a solvent such as methyl t-butyl ether or tetrahydrofuran at e.g. 0°-60° C.); or (5) benzyl: by palladium catalysed hydrogenolysis in an alkanol such as ethanol at or near ambient temperature and pressure or by use of an alkali metal such as sodium in liquid ammonia.

(c) A diol derivative of the formula VI wherein one of $T^1$ and $T^2$ is hydrogen and the other is hydrogen or a group of the formula —$CRaRb.OH$ (wherein Ra and Rb are the same or different (1-4C)alkyl groups) is reacted with an aldehyde derivative of the formula $R^1.CHO$, or an acetal, hemiacetal or hydrate thereof.

The latter aldehyde [or its hydrate, or its acetal or hemi-acetal with a (1-4C)alkanol (such as methanol or ethanol)] may conveniently be present in an excess.

The reaction is generally performed in the presence of an acid such as hydrogen chloride, hydrogen bromide, sulphuric acid, phosphoric acid, methanesulphonic acid or p-toluenesulphonic acid, conveniently in the presence of a suitable solvent or diluent, such as dichloromethane, toluene, xylene or an ether, for example tetrahydrofuran, dibutyl ether, methyl t-butyl ether or 1,2-dimethoxyethane, and at a temperature in the range, for example, 0° to 80° C.

Those starting materials of formula VI wherein $T^1$ and $T^2$ are both hydrogen may be obtained, for example, by mild, acid catalysed, hydrolysis or alcoholysis of the dioxane ring of a compound of formula VII wherein one of Ra and Rb is hydrogen or (1-4C)alkyl (such as methyl or ethyl)and the other is (1-4C)alkyl, obtained by an analogous procedure to process (a) herein, for example, analogous to that described in European patent application, Publication No. 94239. The hydrolysis or alcoholysis will normally be carried out at a temperature in range 10° to 80° C. using an aqueous mineral acid such as hydrochloric acid in an alkanol such as ethanol or 2-propanol or an ether (such as tetrahydrofuran) as solvent.

The starting materials of formula VI wherein one of $T^1$ and $T^2$ is hydrogen and the other is a group of the formula —$CRaRb.OH$ are intermediates in the above-mentioned formation of the starting materials of formula VI wherein $T^1$ and $T^2$ are both hydrogen. However, said intermediates are not normally isolated or characterised. Accordingly, the invention also provides a preferred, modified procedure (d) of process (c) which comprises reacting a 1,3-dioxane of formula VII wherein one of Ra and Rb is hydrogen, methyl or ethyl and the other is methyl or ethyl with an excess of an aldehyde of the formula $R^1.CHO$ (or a hydrate, acetal or hemiacetal thereof) in the presence of an acid (such as one of those given above), conveniently at a temperature in the range, for example, 10° to 80° C. and, optionally in the presence of a suitable solvent or diluent (such as one of those given above).

In some cases, it is necessary to modify procedures (c) and (d) where the aldehyde of formula $R^1.CHO$ is not particularly reactive or tends to form an acyclic hemiacetal when reacted with the compound of the formula VI or VII, for example when 2,2,2-trifluoroacetaldehyde is used for the production of formula I compounds wherein $R^1$ is trifluoromethyl. Thus, a further procedure (e) of the invention comprises reacting a compound of the formula VI wherein $T^2$ is hydrogen and $T^1$ is alkanesulphonyl (especially methanesulphonyl) or arene-sulphonyl (especially benzene- or toluene-sulphonyl) with an aldehyde of the formula $R^1.CHO$ (or a hydrate, acetal or hemiacetal thereof) (for example with 2,2,2-trifluoroacetaldehyde or its hydrate) in the presence of a suitable acid and under the same general conditions as given above for procedure (c), followed by base-catalysed cyclisation of the acyclic intermediate obtained, for example using a suitable base (such as potassium carbonate or sodium hydride) in a suitable solvent or diluent (such as an ether described above) and at a temperature in the range, for example, 20°-50° C. Such a procedure is illustrated in Example 34 hereinafter using a compound of formula VI in which $R^2$ is methoxy, which group is subsequently converted to hydroxy by hydrolysis after formation of the dioxane ring.

The necessary starting alkanesulphonyl or arenesulphonyl esters of formula VI defined above may be conveniently obtained from the corresponding diol of formula VI ($T^1=T^2$=hydrogen) by reaction with one molecular equivalent of the appropriate alkanesulphonyl or arenesulphonyl halide (such as methanesulphonyl chloride or p-toluenesulphonyl chloride) in a suitable solvent or diluent (such as an ether or dichloromethane) at or near ambient temperature and in the presence of a suitable base (such as triethylamine or pyridine).

(f) Decomposing an ester of the formula VIII wherein $R^6$ is (1–6C)alkyl (especially methyl, ethyl, propyl or t-butyl), phenyl or benzyl the latter two optionally bearing 1 or 2 halogeno, (1–4C)alkyl or (1–4C)alkoxy substituents.

The decomposition may be carried out using any one or more of the conventional reagents and conditions well known in the art for converting esters to acids. Thus, for example, the decomposition may conveniently be performed by base catalysed hydrolysis, for example by using an alkali metal hydroxide such as lithium, potassium or sodium hydroxide in an aqueous system conveniently in the presence of a suitable solvent or diluent such as tetrahydrofuran, methanol, ethanol or t-butyl methyl ether and a temperature in the general range, for example, 10° to 60° C. and, conveniently, at or near ambient temperature. Alternatively, when $R^6$ is t-butyl, the decomposition may be carried out thermally by heating the compound of formula VIII at a temperature in the general range, for example, 80° to 150° C., alone or in the presence of a suitable diluent such as diphenylether or diphenylsulphone.

The necessary starting materials for use in the above processes (a)–(f) may be obtained by general procedures well known for the production of structurally related compounds, for example using analogous procedures to those described in European patent no. 94239B1 and patent application no. 98690A2.

The aldehydes of the formula IV may be obtained, for example, from the allyl compounds of formula XI as shown in Schemes 1 and 2 hereinafter and as illustrated in the Examples, it being recognised that when a particular stereoisomer is required, the sequence of selective reductions may need to be manipulated and any mixtures of isomers separated, for example using chromatography. Alternatively, when a particular stereoisomer is required, it may be obtained starting from a specific enantiomer of a 3-[2-(1-hydroxy-1-pyridylmethyl)pent-4-enyl]oxazolidin-2-one of the formula XI in which $R^7$ is (1–4C)alkyl (especially isopropyl) itself obtained from aldol condensation of the corresponding 3-(4-pentenoyl)oxazolidin-2-one with pyridylcarboxaldehyde, as shown in Scheme 3 hereinafter. [This procedure is particularly suitable for obtaining individual enantiomers of the compounds of formula I].

The protected hydroxy derivatives of formula V may be obtained for example by carrying out process (c) or (d) above with a suitable compound analogous to the 1,3-dioxane of formula VII but in which X is a suitably protected hydroxy group, such a compound being itself readily obtainable using standard procedures analogous to those described above and to those set out in the accompanying Examples.

The appropriate diols of formula VI for the production of dioxanes of formula I or VII wherein the pyridyl moiety bearing X and the alkenoic acid side-chain have cis-relative stereochemistry, may be obtained, for example, using an analogous procedure to that described in European patent application, publication no. 142323, starting from the appropriate pyridine-carboxaldehyde and succinic anhydride and a suitable base such as that used in Scheme 3 for the aldol condensation.

The esters of formula VIII may be made, for example, by carrying out process (c) using the appropriate ester of the diol corresponding to formula VI.

The necessary Wittig reagents may be obtained by conventional procedures, for example by treating the corresponding phosphonium halides with a strong base such as sodium hydride, lithium diisopropylamide, potassium t-butoxide or butyllithium. They are generally formed in situ just prior to carrying out the condensation process (a) above.

It will be understood that the compounds of formula I wherein $R^2$ is hydroxy may also be obtained by other conventional procedures well known in the art, for example by base catalysed hydrolysis of the corresponding amides or nitriles. In addition, those compounds of formula I wherein $R^2$ is other than hydroxy may be made by conventional esterification or sulphonamidation procedures from the compounds wherein $R^2$ is hydroxy (or a reactive derivative thereof) and the appropriate alcohol, phenol or (1–4C)alkanesulphonamide. Such procedures are also within the ambit of the invention.

Whereafter, when a salt of a compound of formula I is required, it may be obtained by reaction with the appropriate base or acid affording a physiologically acceptable ion, or by any other conventional salt formation procedure.

Further, when an optically active form of a compound of formula I is required, one of the aforesaid processes may be carried out using an optically active starting material (for example, one described in Scheme 3, as illustrated in Example 40 hereinafter). Alternatively, the racemic form of a compound of formula I may be resolved, for example by reaction with an optically active form of a suitable organic acid or base, for example, camphorsulphonic acid, ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid (or base) using a conventional procedure, for example using an aqueous mineral acid such as dilute hydrochloric acid (or aqueous alkali such as aqueous sodium hydroxide).

In general, the enantiomeric form of the compound of formula I in which the groups on the dioxane ring have the 2S,4S,5R configuration is preferred.

Many of the intermediates defined herein are novel, for example those of formulae IV, V, VI, VII, VIII and IX and XI, and are provided as further, separate features of the invention. It should be noted that in addition certain of the compounds of formula VII (such as those in which Ra and Rb are both methyl or ethyl) possess useful thromboxane $A_2$ synthase inhibitory properties and may themselves be valuable as pharmaceuticals either per se or in the form of pharmaceutical compositions, which are also within the ambit of the invention.

As stated earlier, the compounds of formula I possess significant $TXA_2$ antagonist properties and are inhibitors of $TXA_2$ synthase. The $TXA_2$ antagonism may be demonstrated in one or other of the following standard tests:

(a) The rat aortic strip model analogous to that devised by Piper and Vane (*Nature*, 1969, 223, 29–35) using as agonist the $TXA_2$ mimetic agent known as U46619 (described by R L Jones et alia in "Chemistry, Biochemistry and Pharmacological Activity of Prostanoids" edited by S M Roberts and F Scheinmann, at page 211; Pergamon Press, 1979);

(b) a blood platelet aggregation test based on that described by Born (*Nature*, 1962, 194, 927–929) and involving:
  (i) aggregating human, citrated, platelet-rich plasma by addition of the $TXA_2$ mimetic agent U46619 so that a dose-response curve is generated;
  (ii) generating a dose-response curve for U46619 stimulated platelet aggregation in the presence of increasing amounts of test compound (generally in the range $10^{-5}M$ to $10^{-10}M$); and
  (iii) calculating a $K_B$ value indicating potency of $TXA_2$ antagonism for the test compound, averaged over several concentrations, from the calculated 50% response value for U46619 aggregation in the presence and absence of test compound; or (c) a bronchoconstriction test involving measuring the inhibition by a test compound of the bronchoconstriction induced in Konzett-Rossler, anaesthetised guinea-pig model (as modified by Collier and James, *Brit. J. Pharmacol.*, 1967, 30, 283–307) by intravenous administration of the $TXA_2$ mimetic agent, U46619 and involving:
  (i) obtaining a cumulative dose-response curve to U46619 induced bronchoconstriction by intravenous administration of constant volumes of increasing concentrations of U46619 (0.2–4 μg/kg) in physiological saline solution and expressing bronchoconstriction as the maximum of that theoretically obtainable with no air flow to the test animal;
  (ii) generating a cumulative dose-response curve to U46619 induced bronchoconstriction at 30 minute intervals for 3 hours after oral dosing of test compound; and
  (iii) calculating a dose-ratio for the test compound (that is the ratio of concentration of U46619 required to cause 50% bronchoconstriction in the presence and absence of test compound) indicating the potency of $TXA_2$ antagonism.

Test (b) may conveniently be modified to demonstrate the antagonism of the effects of $TXA_2$ in vivo by assessing the effects of a test compound on the aggregation of blood platelets obtained after administration of test compound to a laboratory animal, such as a rabbit, rat, guinea pig or dog. However, when the aggregation of dog platelets is being studied it is necessary to use a predetermined, threshold concentration of the platelet aggregation agent adenosine diphosphate (about $0.4–1.2\times10^{-6}M$) together with the $TXA_2$ mimetic agent, U46619.

The antagonism of the effects of $TXA_2$ on the vasculature may also be demonstrated, for example in rats in the following procedure:

(d) Male rats (Alderley Park strain) are anaesthetised with sodium pentobarbital and blood pressure is monitored at the carotid artery. The $TXA_2$ mimetic agent U46619 is administered intravenously at 5 μg/kg via the jugular vein to produce 20–30 mm/Hg (2640–3970 pascal) increase in systolic blood pressure. The process is repeated twice to ensure adequacy of response. A test compound is then administered either intravenously (via the jugular vein) or orally (via a cannula) directly into the stomach and the animal challenged with U46619, five minutes after dosing with test compound and then successively every ten minutes until the hypertensive effect of U46619 is no longer blocked.

The $TXA_2$ synthase inhibitory properties of a test compound may be demonstrated using the standard in vitro test procedure [test (e)] described by Howarth et alia (*Biochem. Soc. Transactions*, 1982, 10, 239–240) using a human platelet microsomal $TXA_2$ synthase preparation and using a quantitative thin layer radiochromatographic method to assess the conversion of [1-$^{14}$C]arachidonic acid to the $TXA_2$ metabolite thromboxane $B_2$ ($TXB_2$).

The $TXA_2$ synthase inhibitory properties of a test compound may also be demonstrated in a standard procedure [test (f)] involving obtaining blood samples from laboratory animals (typically rats, but also guinea pigs, rabbits or dogs) dosed with the test compound, generally by the oral route. The samples treated with anticoagulant are first incubated at 37° C. with collagen (at about 100 micro M), then mixed with the cyclooxygenase inhibitor indomethacin (at about $10^{-3}M$), centrifuged and the level of the $TXA_2$ metabolite, $TXB_2$, determined by a standard radioimmunoassay technique. By comparison of the amount of $TXB_2$ present in the plasma from animals dosed with test compound with that in the plasma of a control group dosed with placebo, the $TXA_2$ synthase inhibitory properties may be assessed.

In general, compounds of formula I wherein $R^1$ and $R^2$ are hydroxy show effects in the following ranges in one or more of the above tests:

test (a): $pA_2$ of $>5.5$
test (b): $K_B$ of $<1.5\times10^{-6}M$
test (c): dose ratio of $>5$, 1 hour after dosing at 10 mg/kg
test (d): significant inhibition of U46619 induced hypertension for at least 1 hour following oral dosing at 50 mg/kg or less
test (e): $IC_{50}$ of $<1.0\times10^{-6}M$
test (f): significant inhibition of $TXB_2$ production 1 hour following a dose of 100 mg/kg or less.

No overt toxic or other untoward effects have been observed with representative compounds of formula I having effects in in vivo tests (c), (d) or (f) at several multiples of the minimum effective dose.

Compounds of the formula I wherein $R^2$ is other than hydroxy in general show lower activity in the above in vitro tests but show similar activity to the $R^2$=hydroxy compounds of formula I in the in vivo tests.

By way of illustration, the compound described in Example 2 hereinafter possesses both $TXA_2$ antagonist and $TXA_2$ synthase inhibitory properties as indicated by a $K_B$ of $6.5\times10^{-7}$ in test (b), an $IC_{50}$ of $4.8\times10^{-8}M$ in test (e) and shows up essentially complete inhibition of $TXB_2$ production up to 5 hours following an oral dose of 25 mg/kg to rats in test (f) without any observable signs of toxicity to the test animals.

As stated previously, by virtue of their combined $TXA_2$ antagonist and $TXA_2$ synthase inhibitory properties, the compounds of formula I may be used in the therapy or prevention of diseases or adverse conditions in warm-blooded animals in which $TXA_2$ (or prostaglandins $H_2$, $D_2$ and/or $F_2$ alpha) are involved. In general, a compound of formula I will be administered for this purpose by an oral, rectal, intravenous, subcutaneous, intramuscular or inhalation route, so that a dose in the range, for example 0.01–15 mg/kg body weight, will be given up to four times per day, varying with the route of administration, the severity of the condition and the size and age of the patient under treatment.

The compounds of formula I will generally be used in the form of a pharmaceutical composition comprising a compound of formula I or, a pharmaceutically acceptable salt thereof as defined hereinabove, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example a known platelet aggregation inhibitor, hypolipidemic agent, anti-hypertensive agent, thrombolytic agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition. Still further, a known $TXA_2$ antagonist, such as a preferred compound described in European patent application, Publication No. 201354, or a known $TXA_2$ synthase inhibitor such as dazoxiben or furegrelate [U63557] may be present in addition to a compound of the formula I, or a pharmaceutically acceptable salt thereof, in a composition according to the invention in order to modify the overall balance of $TXA_2$ antagonist and $TXA_2$ synthase inhibitory effects for the required therapeutic effect in any of the aforesaid diseases or disease conditions.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of $TXA_2$ in laboratory animals such as cats, dogs, rabbits, monkeys, rats and mice, as part of the continuing search for new and improved therapeutic agents. The compounds of formula I may also be used because of their $TXA_2$ antagonist and synthase inhibitory properties in helping to maintain the viability of blood and blood vessels in warm-blooded animals (or parts thereof) under-going artificial extracorporeal circulation, for example during limb or organ transplants. When used for this purpose a compound of formula I, or a physiologically acceptable salt thereof, will generally be administered so that a steady state concentration in the range, for example, 0.1 to 10 mg. per liter is achieved in the blood.

The invention will now be illustrated by the following nonlimiting Examples in which, Examples 1 and 17 describe the production of a useful intermediate and, unless otherwise stated:

(i) concentrations and evaporations were carried out by rotary evaporation in vacuo;

(ii) operations were carried out at room temperature, that is in the range 18°–26° C.;

(iii) flash column chromatography was performed on Fluka Kieselgel 60 (catalogue no. 60738) obtained from Fluka AG, Buchs, Switzerland CH-9470;

(iv) yields, where given, are intended for the assistance of the reader only and are not necessarily the maximum attainable by diligent process development;

(v) proton NMR spectra were normally determined at 90 or 200 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multipier; t, triplet; br, broad; d,doublet;

(vi) all end-products were isolated as racemates and had satisfactory microanalyses; and (vii) for convenience, racemic end-products are named using "cis" or "trans" nomenclature to depict the relative configuration of substituents about the dioxane ring i.e. in such racemates, the substituents at positions 4 and 5 are referred to as (4,5-cis) instead of the more precise (4SR,4RS) notation, which latter notation is used in naming the enantiomeric forms described in Example 40 hereinafter.

EXAMPLE 1

A solution of 2-[(4,5-cis)-2,2-dimethyl-4-(3-pyridyl)-1,3-dioxan-5-yl]acetaldehyde (D), (0.20 g) in dry tetrahydrofuran (THF) (7 ml) was added under argon to a stirred, ice-cooled solution of the ylid prepared from (3-carboxypropyl)triphenylphosphonium bromide (0.91 g) and potassium t-butoxide (0.48 g) in dry THF (30 ml). The mixture was stirred for 2 hours and then treated with ice-cooled water (50 ml). The solution was concentrated and more water was added (25 ml). The pH was adjusted to 7 by addition of a few crystals of oxalic acid and the solution was extracted with ethyl acetate (3×40 ml). The aqueous phase was then acidified to pH 4 with oxalic acid and extracted with ethyl acetate (3×50 ml). These combined extracts were washed with saturated brine (50 ml), dried ($MgSO_4$) and concentrated. The residue was purified by flash column chromatography, eluting with dlchloromethane/methanol (95:5, v/v), to give 4(Z)-6-[2,2-dimethyl-4-(3-pyridyl)-1,3-dioxan-cis-5-yl]hexenoic acid as an oil (0.19 g); NMR: 1.55 (3H,s), 1.57 (3H,s), 1.5–2.6 (7H,m), 3.85 (1H,dd, J=12 HZ, 1.5 Hz), 4.15 (1H,dm, J=12 Hz), 5.15–5.50 (3H,m), 7.3–7.4 (1H, m), 7.7–7.8 (1H,m), 8.1 (1H, brs) and 8.45–8.60 (2H, m).

The necessary starting material was prepared as follows:

(i) Methyl 2-(nicotinoyl)acetate (17.9 g, prepared by the method of E Wenkert et al, *J. Org. Chem.*, 1983, 48, 5006) was added under argon to a solution of sodium metal (2.3 g) in methanol (200 ml) and the resulting mixture was stirred at 25° C. for 30 mins. Allyl bromide (12.0 g) was then added and stirring was continued overnight. A further amount (about 2 g) of allyl bromide was added, the mixture was stirred for 48 hours, and then concentrated. The residual oil was partitioned between water and ether and the aqueous layer was extracted three times with ether. The combined extracts were washed with saturated brine, dried (MgSO$_4$) and concentrated. The residue was purified by flash column chromatography, eluting with a mixture of petroleum ether (b.p. 60°–80°) and ethyl acetate (1:1, v/v) to give methyl-2-nicotinoyl-4-pentenoate (A) as a pale yellow oil (13.8 g); NMR 2.6–2.9 (2H,m), 3.7 (3H,s), 4.4 (1H,m), 4.9–5.2 (2H,m), 5.5–6.0 (1H,m), 7.2–7.5 (1H,m), 8.1–8.3 (1H,m), 8.7–8.8 (1H,m) and 9.1–9.2 (1H,m).

(ii) A solution of A (8.8 g) in dry THF (40 ml) was added to suspension of lithium aluminium hydride (1.8 g) in dry THF (80 ml) under argon at such a rate that the temperature did not exceed 10° C. After 2 hours the mixture was cooled in ice. Ethyl acetate (20 ml) was then added to destroy excess reagent, followed by saturated aqueous ammonium chloride (50 ml). The precipitate was removed by filtration and washed with ethyl acetate. The aqueous phase was separated and extracted with ethyl acetate (3×50 ml). The combined organic fractions were washed with saturated brine, dried (MgSO$_4$) and concentrated. The residue was purified by flash column chromatography, eluting with a mixture of ethyl acetate and methanol, (95:5 v/v), to give 2-allyl-1-(3-pyridyl)-1,3-propanediol (B) (5.3 g), as an oil (mixture of epimers); NMR: 1.8–2.2 (3H,m), 3.6–4.1 (4H,m), 4.7–5.2 (3H,m), 5.6–5.9 (1H,m), 7.2–7.4 (1H,m), 7.65–7.8 (1H,m) and 8.4–8.6 (2H,m).

(iii) A mixture of B (5.2 g), p-toluenesulphonic acid (5.2 g), and 2,2-dimethoxypropane (50 ml), was stirred overnight at room temperature. The pH was adjusted to 8–10 by addition of triethylamine and the solution was concentrated under reduced pressure. The residue was purified by flash column chromatography, eluting with a mixture of petroleum ether (b.p. 40°–60°) and ethyl acetate (60:40 v/v) to give 5-allyl-2,2-dimethyl-4-(3-pyridyl)-1,3-dioxane (C) (mixture of 4,5-cis and trans isomers) as an oil (4.6 g); NMR: 1.4–1.6 (6H,m), 1.6–2.5 (3H,m), 3.65–4.25 (2H,m), 4.5–5.7 (4H,m), 7.2–7.4 (1H,m), 7.6–7.8 (1H,m) and 8.45–8.65 (2H,m).

(iv) Ozone in oxygen was bubbled through a solution of C (3.4 g), in ethyl acetate (130 ml) at −70° C. until a blue colour persisted thoughout. Argon was then bubbled through the solution to discharge the excess ozone and a solution of triphenylphosphine (6 g) in ethyl acetate (50 ml) was added. The mixture was allowed to warm to room temperature and then stirred overnight. The solution was concentrated and ether (50 ml) was added to precipitate triphenylphosphine oxide. The mixture was filtered and the filtrate was concentrated to give an oil which was purified by flash column chromatography, eluting with a mixture (60:40 v/v) of ethyl acetate and petroleum ether (b.p. 40°–60°) to give initially 2-[(4,5-cis]-2,2-dimethyl-4-(3-pyridyl)-1,3-dioxan-5-yl]acetaldehyde (D) as an oil (0.8 g); NMR: 1.5 (3H,s), 1.55 (3H,s), 2.0–2.3 (1H,m), 2.3–2.5(1H,m), 2.8–3.0 (1H,m), 3.8 (1H,dd, J=12 Hz, 1.5 Hz), 4.3 (1H,dm, J=12 Hz), 5.25 (1H,d, J=3 Hz), 7.25–7.35 (1H,m), 8.45–8.60 (2H,m) and 9.6 (1H,s); and then the corresponding 4,5-trans isomer; NMR: 1.47 (3H,s), 1.57 (3H,s), 2.0–2.6 (3H,m), 3.75–4.05 (2H,m), 4.68 (1H,d, J=10 Hz), 7.25–7.40 (1H,m), 7.70–7.80 (1H,m), 8.50–8.65 (2H,m) and 9.5 (1H,br s); as an oil (0.7 g).

EXAMPLE 2

A mixture of 4(Z)-6-[2,2-dimethyl-4-(3-pyridyl)-1,3-dioxan-cis-5yl]hexenoic acid (0.458 g), 2-chlorobenzaldehyde, (0.84 ml), and p-toluenesulphonic acid, (0.314 g), was stirred at 25° C. for 60 hours. The solution was made basic by addition of triethylamine and the entire reaction mixture was then purified by flash column chromatography, eluting first with dichloromethane to give unreacted aldehyde and second with dichloromethane/methanol (95:5, v/v) to give 4(Z)-6-[(2,4,5-cis)-2-(2-chlorophenyl)-4-(3-pyridyl)-1,3-dioxan-5-yl]hexenoic acid (0.16 g), as an oil; NMR: 1.6–2.7 (7H,m), 4.1–4.4 (2H,m), 5.20–5.55 (3H,m), 6.05 (1H,s), 7.2–7.5 (5H,m), 7.65–7.95 (2H,m) and 8.4–8.6 (2H,m).

EXAMPLE 3

Using an analogous procedure to that described in Example 2 but starting from 5(Z)-7-[2,2-dimethyl-4-(3-pyridyl)-1,3-dioxan-cis-5-yl)heptenoic acid (E) and 2-chlorobenzaldehyde, there was obtained 5(Z)-7-[(2,4,5-cis)-2-(2-chlorophenyl)-4-(3-pyridyl)-1,3-dioxan-5-yl]heptenoic acid as an oil in 47% yield; NMR: 1.5–2.7 (9H,m), 4.1–4.4 (2H,m), 5.2–5.5 (3H,m), 6.05 (1H,s), 7.2–7.5 (5H,m), 7.7–7.9 (2H,m) and 8.45–8.65 (2H,m).

The starting heptenoic acid (E) was obtained using an analogous procedure to that described in Example 1 for the corresponding hexenoic acid, except that (4-carboxybutyl)triphenylphosphonium bromide was used in place of (3-carboxypropyl)triphenylphosphonium bromide. The heptenoic acid (E) was obtained as an oil in 40% yield; NMR: 1.55 (3H,s), 1.57 (3H,s), 1.5–2.6 (9H,m), 3.85 (1H,dd, J=12 Hz; 1.5 Hz), 4.15 (1H,dm J=12 Hz), 5.15–5.50 (3H,m), 6.6 (1H, brs), 7.3–7.4 (1H,m), 7.7–7.8 (1H,m) and 8.45–8.60 (2H,m).

EXAMPLE 4

Using a similar procedure to that described in Example 2, but starting from 2-phenoxy-2-methylpropanal instead of 2-chlorobenzaldehyde, there was obtained 4(Z)-6-[(2,4,5-cis)-2-(1-methyl-1-phenoxyethyl)-4-(3-pyridyl)-1,3-dioxan-5-yl]hexenoic acid as a colourless oil (28% yield), which solidified on standing; NMR: 1.35 (3H,s), 1.40 (3H,s), 1.5–2.6 (7H,m), 3.9–4.3 (2H,m), 4.75 (1H,s), 5.1 (1H,d, J=2 Hz), 5.15–5.55 (2H,m), 6.95–7.15 (3H,m), 7.2–7.4 (3H,m), 7.60–7.75 (1H,m) and 8.5–8.6 (2H,m).

The starting aldehyde was prepared as described in European patent application, publication no. 201351 A2, Example 6.

EXAMPLE 5

3-Pyridinecarboxaldehyde (0,365 ml) and p-toluenesulphonic acid (1.08 g) were added to a solution of 4(Z)-6-[2,2-dimethyl-4-(3-pyridyl)-1,3-dioxan-cis-5-yl]hexenoic acid (0.393 g) in acetonitrile (8 ml), under an atmosphere of argon. The mixture was heated at reflux for 4 hours and then allowed to cool. Ethyl acetate (10 ml) was added and the mixture was extracted with 1M sodium hydroxide solution (50 ml). The combined extracts were acidified to pH 4 with acetic acid and extracted with ethyl acetate (4×20 ml). The combined organic extracts were dried (MgSO$_4$), and concentrated to give an oil, which was purified by flash column chromatography, eluting with methanol/dichloromethane (1:10 to 1:5 v/v), to give 4(Z)-6-[(2,4,5-cis)-2,4-bis-(3-pyridyl)-1,3-dioxan-5-yl]hexenoic acid, (0.231 g) as an oil; NMR: 1.6–1.9(2H,m), 2.3–2.7(5H,m), 4.1–4.35(2H,m), 5.2–5.55(3H,m), 5.8(1H,s), 7.3–7.4(2H,m), 7.9–8.0(1H,m) and 8.5–8.85(4H,m).

EXAMPLES 6–16

Using an analogous procedure to that described in Example 5, but replacing 3-pyridinecarboxaldehyde by the appropriate aldehyde of the formula R$^4$.CHO, the following acids of the formula III (A$^3$=ethylene) were obtained as oils in yields of 14–86%:

washed with water (2×25 ml), saturated brine (25 ml), dried (MgSO$_4$) and evaporated. Purification by flash chromatography eluting with ether/hexane (1:1 v/v) gave ethyl 2-methyl-2-(3-pyridyloxy)propionate (A) as a clear oil (34%); NMR: 1.27 (3H,t,J=7 Hz), 1.61 (6H,s), 4.25 (2H,q,J=7 Hz), 7.19 (2H,m), 8.27 (2H,m).

(ii) A 1.5M solution of diisobutylaluminium hydride in toluene (21 ml) was added dropwise under argon to a stirred solution of A (2.09 g) in toluene (75 ml) at −70° C. Stirring was continued for 5 minutes after the addition was complete and then a 10% v/v solution of methanol in toluene (15 ml) was added. The mixture obtained was added to water (300 ml), vigor-

| Example | R$^4$ | $^1$H NMR (ppm) |
|---|---|---|
| 6 | (CH$_3$)$_3$CH— | 1.0(9H, s), 1.5–1.75(2H, m), 2.2–2.55(5H, m), 3.85–3.95(1H, m), 4.1–4.2(1H, m), 4.35(1H, s), 5.0–5.5(3H, m), 7.3–7.4(1H, m), 7.7–7.75(1H, m), 8.5–8.6(2H, m). |
| 7 | 3-Py.O.C(CH$_3$)$_2$— | 1.4(3H, s), 1.43(3H, s), 1.5–1.8(2H, m), 2.2–2.6(5H, m), 3.95–4.3(2H, m), 4.8(1H, s), 5.1–5.55(3H, m), 7.2–7.7(4H, m), 8.3–8.6(4H, m). |
| 8 | 4CN—Ph | 1.45–2.6(7H, m), 4.05–4.25(2H, m), 5.15–5.45(3H, m), 5.9(1H, s), 7.35–7.45(1H, m), 7.7–7.9(5H, m), 8.5–8.6(2H, m). |
| 9 | 2CN—Ph | 1.5–2.7(7H, m), 4.1–4.3(2H, m), 5.15–5.5(3H, m), 6.0(1H, s), 7.35–7.95(6H, m), 8.45–8.6(2H, m). |
| 10 | 3Br—PhO.C(CH$_3$)$_2$— | 1.38(3H, s), 1.42(3H, s), 1.5–1.8(2H, m), 2.2–2.6(5H, m), 3.95–4.25(2H, m), 4.75(1H, s), 5.1–5.55(3H, m), 6.9–7.75(6H, m), 8.5–8.6(2H, m). |
| 11 | 4Br—PhO.C(CH$_3$)$_2$— | 1.37(3H, s), 1.4(3H, s), 1.5–1.8(2H, m), 3.95–4.25(2H, m), 4.75(1H, s), 5.05–5.5(3H, m), 6.9–7.7(6H, m), 8.5–8.6(2H, m). |
| 12 | 4F—PhO.C(CH$_3$)$_2$— | 1.35(3H, s), 1.4(3H, s), 1.55–1.8(2H, m), 2.2–2.6(5H, m), 3.95–4.25(2H, m), 4.75(1H, s), 5.05–5.5(3H, m), 6.85–7.05(4H, m), 7.3–7.7(2H, m), 8.5–8.6(2H, m). |
| 13 | 3F—PhO.C(CH$_3$)$_2$— | 1.38(3H, s), 1.42(3H, s), 1.55–1.8(2H, m), 2.2–2.55(5H, m), 3.95–4.25(2H, m), 4.8(1H, s), 5.1–5.5(3H, m), 6.75–6.85(3H, m), 7.15–7.75(3H, m), 8.5–8.6(2H, m). |
| 14 | PhCH$_2$.C(CH$_3$)$_2$— | 1.0(6H, s), 1.55–1.75(2H, m), 2.25–2.55(5H, m), 2.75(2H, s), 3.85–4.2(2H, m), 4.3(1H, s), 5.0–5.5(3H, m), 7.1–7.75(7H, m), 8.5–8.6(2H, m). |
| 15 | 4CN—PhO.C(CH$_3$)$_2$— | 1.43(3H, s), 1.46(3H, s), 1.55–1.8(2H, m), 2.2–2.55(5H, m), 3.95–4.25(2H, m), 4.8(1H, s), 5.1–5.5(3H, m), 7.1–7.75(6H, m), 8.5–8.6(2H, m). |
| 16 | 2NO$_2$—Ph.CH=CH— | 1.6–1.85(2H, m), 2.2–2.9(5H, m), 4.05–4.3(2H, m), 5.15–5.5(4H, m), 6.25–6.35(1H, m), 7.3–8.0(7H, m), 8.5–8.6(2H, m). |

[Note: Py = Pyridyl and Ph = Phenyl, optionally substituted as indicated]

The starting aldehyde for Example 7, 2-methyl-2-(3-pyridyloxy)propionaldehyde, was prepared as follows:
(i) A solution of 3-hydroxypyridine (4.75 g) in 1,3-dimethyl-3,4,5,6-tetrahydro-2(1H)-pyrimidinone (DMPU) (10 ml) was added dropwise over 30 minutes to a stirred, ice-cooled, suspension of sodium hydride (50% w/w dispersion in mineral oil, 2.4 g) in DMPU (40 ml). The mixture was heated to 50° C. to give a clear solution and then cooled to 4° C. Ethyl 2-bromo-2-methylpropionate (4.38 ml) and potassium iodide (100 mg) were next added and the mixture stirred at ambient temperature for 16 hours. The mixture was poured into water (50 ml) and extracted with ether (3×50 ml). The combined extracts were ously stirred for 30 minutes and then filtered through kieselguhr. The organic phase was separated and the aqueous phase was saturated with sodium chloride and then extracted with ether (2×100 ml). The combined organic phases were washed with saturated brine (3×100 ml), then dried (MgSO$_4$) and evaporated. Purification of the residue by MPLC, eluting with ethyl acetate/hexane (1:1 v/v), gave 2-methyl-2-(3-pyridyloxy)propionaldehyde as a clear oil (56%); NMR: 1.46 (6H,s), 7.20 (2H,m), 8.31 (2H,m), 9.34 (1H,s).

The starting aldehyde for Example 10, 2-(3-bromophenoxy)-2-methylpropanal, was prepared as follows:

(i) A solution of methyl dichloroacetate (77.18 g, 0.54 mol) in anhydrous ether (50 ml) was added to a stirred solution of methyl magnesium iodide [prepared from magnesium turnings (32.8 g, 1.35 mol) and methyl iodide (84.1 ml, 1.35mol)] in anhydrous ether (750 ml) at 0° C. under an argon atmosphere, at such a rate that the temperature did not rise above 15° C. The mixture was stirred at 25° C. for 30 minutes then cooled to 0° C. Water (100 ml) was added and the mixture was acidified to pH4 with concentrated hydrochloric acid. The organic phase was separated and the aqueous phase extracted with ether (3×100 ml). The combined organic phases were dried (MgSO$_4$) and concentrated. The residual oil was distilled under reduced pressure to give 1,1-dichloro-2-hydroxy2-methylpropane (A) (57.81 g), as an oil; b.p. 48°–50° C. at 20 mmHg; NMR: 1.45 (6H,s), 2.15 (1H,br s) and 5.65 (1H,s).

(ii) Cetyltrimethyl ammonium bromide (0.28 g, 0.77 mmol) was added to a solution of m-bromophenol (6.66 g, 38.5 mmol) in 3.85M aqueous sodium hydroxide solution (10 ml), followed by a solution of A (1.37 g, 9.6 mmol) in ether (20 ml). The mixture was stirred under an argon atmosphere for 18 hours then diluted with ether (50 ml), and extracted with 2M aqueous sodium hydroxide solution (4×30 ml), to remove unreacted phenol. The combined aqueous extracts were extracted with ether (50 ml), and the organic phase was washed with 2M aqueous sodium hydroxide solution (20 ml) followed by water (50 ml). The combined organic phases were dried (MgSO$_4$), concentrated, and purified by flash column chromatography, eluting with ethyl acetate/hexane (1:10 v/v), to give 2-(3-bromophenoxy)-2-methylpropanal (0.89 g), as an oil; NMR: 1.45 (6H,s), 6.75–7.20 (4H,m), 9.8 (1H,s).

Using an analogous procedure to that described for the preparation of 2-(3-bromophenoxy)-2-methylpropanal, but starting from the appropriately substituted phenol, the following aldehydes used in Examples 11, 12, 13, and 15 were obtained:
2-(4-bromophenoxy)-2-methylpropanal; NMR: 1.4 (6H,s), 6.7–7.4 (4H,m), 9.8 (1H,s);
2-(4-fluorophenoxy)-2-methylpropanal; NMR: 1.4 (6H,s), 6.8–7.0 (4H,m), 9.8 (1H,s);
2-(3-fluorophenoxy)-2-methylpropanal NMR: 1.45 (6H,s), 6.55–7.3 (4H,m), 9.8 (1H,s); and
2-(4-cyanophenoxy)-2-methylpropanal; NMR: 1.5 (6H,s), 6.85–7.6 (4H,m), 9.75 (1H,s).

The starting aldehyde for Example 14 was prepared by the method described of H K Diefl and K C Brannock, Tetrahedron Letters, 1973, 14, 1273.

EXAMPLE 17

Using an analogous procedure to that described in Example 1 but starting from 2-[(4,5-cis)-2,2-dimethyl-4-(4-pyridyl)-1,3-dioxan-5-yl]acetaldehyde, there was obtained 4(Z)-6-[2,2-dimethyl-4-(4-pyridyl)-1,3-dioxan-cis-5-yl]hexenoic acid as an oil, which solidified on standing, in 7% yield; m.p. 167°–169° C. (after recrystallisation from ethyl acetate/petroleum ether); NMR: 1.42(3H,s), 1.49(3H,s), 1.7–2.5(7H,m), 3.66(1H,d,J=12 Hz), 4.12(1H,d,J=12 Hz), 5.1–5.42(3H,m), 7.30(2H,d), and 8.52(2H,d).

The above starting material was obtained as an oil, in 50% yield, using an analogous procedure to that described in Example 1; NMR: 1.5 (3H,s), 1.55 (3H,s), 2.0–2.3 (1H,m), 2.3–2.5 (1H,m), 2.8–3.0 (1H,m), 3.8 (1H,dd,J=12 Hz, 1.5 Hz), 4.3 (1H, dm,J=12 Hz), 5.2 (1H,d,J=3 Hz), 7.25 (2H,d), 8.6 (2H,d) and 9.62 (1H,s); starting from methyl 3-(4-pyridyl)-3-oxo-propionate, which was prepared using a similar procedure to that of E. Wenkert et al, *J. Org. Chem.*, 1983, 48, 5006.

The following intermediates analogous to those in Example 1 were obtained as oils and used without further purification:
(i) Methyl-2-isonicotinoyl-4-pentenoate, in 65% yield.
(ii) 2-Allyl-1-(4-pyridyl)-1,3-propanediol, in 77% yield.
(iii) 5-Allyl-2,2-dimethyl-4-(4-pyridyl)-1,3-dioxane (mixture of 4,5-cis and trans isomers), in 44% yield.

EXAMPLE 18

Using an analogous procedure to that described in Example 5 but starting from 4(Z)-6-[2,2-dimethyl-4-(4-pyridyl)-1,3-dioxan-cis-5-yl]hexenoic acid and 2-chlorobenzaldehyde, there was obtained 4(Z)-6-[(2,4,5-cis)-2-(2-chlorophenyl)-4-(4-pyridyl)-1,3-dioxan-5-yl]hexenoic acid as an oil, in 21% yield; NMR: 1.6–2.7 (7H,m), 3.59 (1H,d,J=10.7 Hz), 4.35 (1H,dd,J=10.7 Hz, 4.8 Hz), 4.6 (1H,d,J=10.7 Hz), 5.18–5.5 (2H,m), 5.98 (1H,s), 7.2–7.8 (6H,m) and 8.63 (2H,br s).

EXAMPLES 19–29

Using an analogous procedure to that described in Example 5, but replacing 3-pyridinecarboxaldehyde by the appropriate aldehyde of the formula R$^4$.CHO, the following acids of the formula III (A$^3$=ethylene) were obtained.

| Example | R$^4$ | $^1$H NMR (ppm) |
| --- | --- | --- |
| 19 | 4NO$_2$—Ph | 1.5–2.6(7H, m), 4.1–4.3(2H, m), 5.15–5.5(3H, m), 5.95(1H, s), 7.35–8.6(8H, m). |
| 20 | 2,4-Cl$_2$—Ph | 1.5–2.5(7H, m), 4.05–4.25(2H, m), 5.15–5.45(3H, m), 6.05(1H, s), 7.35–7.85(5H, m), 8.45–8.55(2H, m). |
| 21 | 3,4-Cl$_2$—Ph | 1.6–2.65(7H, m), 4.05–4.3(2H, m), 5.2–5.5(3H, m), 5.7(1H, s), 7.3–7.8(5H, m), 8.5–8.65(2H, m). |
| 22 | 2-Cl,5-NO$_2$—Ph | 1.7–2.7(7H, m), 4.15–4.4(2H, m), 5.2–5.55(3H, m), 6.05(1H, s), 7.3–8.7(7H, m). |
| 23 | 3Br—PhCH$_2$C(CH$_3$)$_2$— | 1.0(6H, s), 1.5–1.75(2H, m), 2.3–2.8(7H, m), 3.8–4.2(2H, m), 4.25(1H, s), 4.95–5.5(3H, m), 7.05–7.4(5H, m), 7.65–7.7(1H, m), 8.5–8.6(2H, m). |
| 24 | 3,4-Cl$_2$—PhO.C(CH$_3$)$_2$— | 1.38(3H, s), 1.4(3H, s), 1.6–1.8(2H, m), 2.2–2.6(5H, m), 3.95–4.25(2H, m), 4.75(1H, s), 5.1– |

-continued

| Example | R⁴ | ¹H NMR (ppm) |
|---|---|---|
|  |  | 5.5(3H, m), 6.9–7.75(5H, m), 8.5–8.6(2H, m). |
| 25 | 4F—PhCH₂C(CH₃)₂— | 1.0(6H, s), 1.55–1.75(2H, m), 2.2–2.55(5H, m), 2.7(2H, s), 3.8–4.2(2H, m), 4.3(1H, s), 4.95–5.5(3H, m), 6.9–7.75(6H, m), 8.5–8.65(2H, m). |
| 26 | 4NO₂—PhO.C(CH₃)₂— | 1.45(6H, s), 1.8–2.5(7H, m), 3.95–4.1(2H, m), 4.9(1H, s), 5.05–5.5(3H, m), 7.2–7.7(4H, m), 8.1–8.2(2H, m), 8.45–8.5(2H, m). |
| 27 | 2F—PhO.C(CH₃)₂— | 1.38(3H, s), 1.42(3H, s), 1.55–1.8(2H, m), 2.2–2.55(5H, m), 3.95–4.3(2H, m), 4.85(1H, s), 5.1–5.5(3H, m), 6.95–7.7(6H, m), 8.45–8.6(2H, m). |
| 28 | 3, 4-F₂—PhO.C(CH₃)₂— | 1.35(3H, s), 1.38(3H, s), 1.55–1.8(2H, m), 2.2–2.55(5H, m), 3.95–4.25(2H, m), 4.75(1H, s), 5.1–5.5(3H, m), 6.7–7.75(5H, m), 8.5–8.6(2H, m). |
| 29 | 4CF₃—Ph | 1.6–2.65(7H, m), 4.15–4.35(2H, m), 5.2–5.5(3H, m), 5.78(1H, s), 7.3–7.8(6H, m), 8.5–8.7(2H, m). |

Using an analogous procedure to that described by R Subramanian, *Chem. and Ind.*, 1978, page 731, for the preparation of 2,2-dimethyl-3-phenylpropanal, but starting from the appropriately substituted benzyl halide, the following aldehydes used in Examples 23 and 25 were obtained:

3-(3-bromophenyl)-2,2-dimethylpropanal; NMR: 1.05(6H,s), 2.75(2H,s), 7.0–7.4(4H,m), 9.55(1H,s);

3-(4-fluorophenyl)-2,2-dimethylpropanal; NMR: 1.05 (6H, s), 2.75 (2H, s), 6.9–7.1(4H,m), 9.55(1H,s);

Using an analogous procedure to that described for the preparation of 2-(3-bromophenoxy)-2-methylpropanal, but starting from the appropiately substituted phenol, the following aldehydes used in Examples 24, 27 and 28 were obtained:

2-(3,4-dichlorophenoxy)-2-methylpropanal; NMR: 1.45(6H,s), 6.7–7.35(3H,m), 9.75(1H,s);

2-(2-fluorophenoxy)-2-methylpropanal; NMR: 1.4(6H,s), 6.9–7.15(4H,m), 9.85(1H,s).

2-(3,4-difluorophenoxy)-2-methylpropanal; NMR: 1.4(6H,s), 6.55–7.1(3H,m), 9.8(1H,s).

The starting aldehyde for Example 26, 2-(4-nitrophenoxy)-2-methylpropanal, was prepared using an analogous procedure to that described for the preparation of 2-methyl-2-(3-pyridyloxy)propionaldehyde, using 4-nitrophenol instead of 3-hydroxypyridine; NMR: 1.55(6H,s), 6.9(2H,d,J=7 Hz), 8.15(2H,d,J=7 Hz), 9.8(1H,s).

EXAMPLE 30 p-Toluenesulphonic acid (0.33 g) was added to a solution of 4(Z)-6-[2,2-dimethyl-4-(3-pyridyl)-1,3-dioxan-cis-5-yl]hexenoic acid (0.482 g) in acetonitrile (15 ml) and the mixture was stirred for 30 minutes. 2-phenoxyacetaldehyde diethyl acetal (1.04 g) was added and the mixture was heated at 90° C. for 15 hours. The mixture was then allowed to cool and concentrated. The residual oil, which contained the required acid product together with its ethyl ester, was dissolved in methanol (6 ml). Aqueous 2M sodium hydroxide solution (3 ml) was added and the mixture was stirred for 1 hour. Ethyl acetate (25 ml) and water (25 ml) were added and the mixture was acidified with acetic acid and extracted with ethyl acetate (4×25 ml). The combined organic extracts were dried (MgSO₄), and concentrated. The resultant oil was purified by flash column chromatography, eluting with dichloromethane and increasing to methanol/dichloromethane (7:93 v/v), to give 4(Z)-6-[(2,4,5-cis)-2-phenoxymethyl-4-(3-pyridyl)-1,3-dioxan-5-yl]hexenoic acid (0.146 g) as an oil; NMR: 1.65–1.85(2H,m), 2.2–2.6(5H,m), 4.0–4.25(4H,m), 5.1–5.45(4H,m), 6.9–7.45(6H,m), 7.75–7.8(1H,m) and 8.5–8.6(2H,m).

The starting material, 2-phenoxyacetaldehyde diethyl acetal, was obtained as follows:

Sodium hydride (5.83 g of a 55% dispersion in mineral oil) was added to a solution of phenol (12.56 g) in DMPU (25 ml) at 5° C. and the mixture was stirred for 30 minutes. Bromoacetaldehyde diethyl acetal (10.05 ml) was added and the mixture was heated at 110° C. for 5 hours, then allowed to cool. The mixture was partitioned between ethyl acetate (100 ml) and water (100 ml) and the organic phase was separated and washed sequentially with aqueous 2M sodium hydroxide solution (2×50 ml) and water (50 ml). The aqueous fractions were combined and re-extracted with ethyl acetate (100 ml). The combined organic extracts were dried (MgSO₄) and concentrated. The resultant oil was purified by flash column chromatography, eluting with ethyl acetate/hexane (1:10 v/v) to give 2-phenoxyacetaldehyde diethyl acetal (9.43 g) as an oil; NMR: 1.25(6H,t, J=7.0 Hz), 3.6–3.85(4H,m), 4.05(2H,d, J=6.0 Hz), 4.85 (1H,t, J=6.0 Hz) and 6.9–7.35(5H,m).

EXAMPLE 31 p-Toluenesulphonic acid (0.358 g) was added to a solution of 4(Z)-6-[2,2-dimethyl-4-(3-pyridyl)-1,3-dioxan-cis-5-yl]hexenoic acid (0.522 g) in acetonitrile (12 ml) and the mixture was stirred for 30 minutes. A solution of 2-(3,4-difluorophenoxy)-2-methylpropanal (1.02 g) in acetonitrile (5 ml) was added, followed by trimethyl orthoformate (0.21 ml), and the mixture was heated at reflux for 3 hours under an atmosphere of argon. To effect complete esterification, methanol (1 ml) was added and the solution was heated at reflux for a further 2 hours.

The reaction mixture was allowed to cool and partitioned between aqueous 1M sodium hydroxide solution (2 ml) and ethyl acetate (25 ml). The organic phase was separated, dried (MgSO$_4$), and concentrated. The resultant oil was purified by flash column chromatography, eluting with methanol/dichloromethane (1:100 to 1:20, v/v), to give methyl 4(Z)-6-[(2,4,5-cis)-2-(1-methyl-1-(3,4-difluorophenoxy)ethyl)-4-(3-pyridyl)-1,3-dioxan-5-yl]hexenoate (0.333 g), as an oil; NMR: 1.37(3H,s), 1.40(3H,s), 1.5–1.8(2H,m), 2.2–2.6(5H,m), 3.65(3H,s), 3.9–4.3(2H,m), 4.75(1H,s), 5.05–5.5(3H,m), 6.7–7.7(5H,m) and 8.5–8.6(2H,m).

EXAMPLE 32

A mixture of 4(Z)-6-[2,2-dimethyl-4-(3-pyridyl)-1,3-dioxan-cis-5-yl]hexenoic acid (0.500 g), 2-methyl-2-propoxypropionaldehyde (2.13 g) and p-toluenesulphonic acid monohydrate (0.342 g) was stirred for 18 hours. 0.2M Sodium hydroxide solution (20 ml) was added and the mixture was washed with ether (2×10 ml), acidified to pH 5 with acetic acid, and then extracted with ether (3×25 ml). The combined ether extracts were washed with water (2×10 ml), saturated sodium chloride solution (10 ml), and dried (MgSO$_4$). The organic extracts were concentrated to give a brown oil, which was purified by medium pressure liquid chromatography (MPLC), eluting with ethyl acetate/hexane/acetic acid (80:20:1 v/v), to give a clear oil which on trituration with ether gave 4(Z)-6-[(2,4,5-cis)-2-(1-methyl-1-propoxyethyl)-4-(3-pyridyl)-1,3-dioxan-5-yl]hexenoic acid, 0.25 hydrate (0.053 g) as a solid, m.p. 116°–118° C.; NMR (200 MHz, d$_6$ DMSO): 0.83(3H,t, J=7 Hz), 1.18(3H,s), 1.20(3H,s), 1.42(3H,m), 1.84(1H,m), 2.14(4H,m), 2.35(1H,m), 3.40(2H,t, J=6 Hz), 3.94(2H,m), 4.65(1H,s), 5.15(1H,d, J=2 Hz), 5.18(1H,m), 5.34(1H,m), 7.38(1H,m), 7.68(1H,dm, J=7 Hz), 8.49(2H,m); microanalysis, found: C,65.8; H,8.3; N,3.7%; C$_{21}$H$_{31}$NO$_5$, 0.25 H$_2$O requires: C, 66.0; H,8.3; N,3.7%.

The starting aldehyde was prepared as described in European patent application, publication no. 201351 A2, Example 7.

EXAMPLE 33

Using an analogous procedure to that described in Example 5, but replacing 3-pyridinecarboxaldehyde with cyclohexanecarboxaldehyde, and carrying out the reaction at ambient temperature in the presence of only 1.1 equivalents of p-toluenesulphonic acid monohydrate, there was obtained 4(Z)-6-[(2,4,5-cis)-2-cyclohexyl-4-(3-pyridyl)-1,3-dioxan-5-yl]hexenoic acid hydrate as a white solid (47% yield), m.p. 121°–125° C. NMR (200 MHz, CDCl3): 1.22 (5H,m), 1.74(8H,m), 2.29(4H,m), 2.44(1H,m), 3.89(1H,d, J=11 Hz), 4.12 (1H,d, J=11 Hz), 4.51(1H,d, J=4 Hz), 5.00 (1H,d, J=1.5 Hz), 5.22(1H,m), 5.38(1H,m), 7.33(1H,m), 7.72(1H,d, J=7 Hz), 8.53(2H,m); microanalysis, founds C,67.2 H,8.1 N,3.7%; C$_{21}$H$_{29}$NO$_4$, 1H$_2$O requires: C,66.8; H,8.2; N,3.7%.

EXAMPLE 34

1M Sodium hydroxide solution (6.28 ml) was added to a stirred solution of methyl 4(Z)-6-[(2,4,5-cis)-4-(3-pyridyl)-2-trifluoromethyl-1,3-dioxan-5-yl]hexenoate (A) (563 mg) in methanol (10 ml). After 2 hours, water (40 ml) was added and the mixture was washed with ether (2×20 ml), acidified to pH 5 with acetic acid, and then extracted with ethyl acetate (3×30 ml). The combined organic extracts were washed with water (20 ml), saturated sodium chloride solution (2×20 ml), and then dried (MgSO$_4$). The solvent was removed by evaporation to give an oil which was purified by MPLC, eluting with ethyl acetate/methanol/acetic acid (95:5:1 v/v) to give 4(Z)-6-[(2,4,5-cis)-4-(3-pyridyl)-2-trifluoromethyl-1,3-dioxan-5-yl]hexenoic acid monoacetate adduct as an oil (587 mg); NMR (200 MHz, CDCl$_3$): 1.71(1H,m), 1.83(1H,m), 2.10(3H,s), 2.30(4H,m), 2.51(1H,m), 4.05(1H,dm, J=11 Hz), 4.30(1H,d, J=11 Hz), 5.12(1H,q, J=3 Hz), 5.20(1H,d, J=2 Hz), 5.22(1H,m), 5.46(1H,m), 7.42(1H,m), 7.80(1H,d, J=7 Hz), 8.59(2H,b); microanalysis, found: C,53.3; H,5.6; N,3.4%; C$_{16}$H$_{18}$NO$_4$F$_3$, 1CH$_3$COOH requires: C,53.5; H,5.4; N,3.5%.

The necessary starting material A was prepared as follows:

(i) 1M Hydrochloric acid (10 ml) was added to a solution of 4(Z)-6-[2,2-dimethyl-4-(3-pyridyl)-1,3-dioxan-cis-5-yl]hexenoic acid (1.42 g) in THF (15 ml) and the mixture was stirred for 2 hours. Water (40 ml) was added and the pH adjusted to 12 with 2M sodium hydroxide solution. The mixture was washed with ethyl acetate (2×25 ml), acidified to pH 5 with acetic acid, and then saturated with solid sodium chloride. The aqueous mixture was then extracted with ethyl acetate (12×50 ml) and the combined extracts were dried (MgSO$_4$). The solvent was removed by evaporation to give 4(Z)-erythro-8-hydroxy-7-hydroxymethyl-8-(3-pyridyl)-4-octenoic acid (B) as a brown oil (1.114 g), which was used without further purification. For the purposes of characterisation, a sample was purified by flash chromatography eluting with methanol/dichloromethane (1:5 v/v); NMR (200 MHz, CDCl$_3$): 1.91(3H,m), 2.23(5H,m), 3.59(2H,m), 5.02(1H,m), 5.35(3H,m), 7.30(1H,m), 7.76(1H,m), 8.46(1H,dd,J=4 and 1 Hz), 8.60(1H,d,J=2 Hz).

(ii) p-Toluenesulphonic acid monohydrate (1.06 g) was added to a solution of B (1.114 g) in methanol (25 ml) and the mixture was stirred for 3 hours. Triethylamine (0.83 ml) was added and the mixture was concentrated to a small volume. Saturated sodium chloride solution (20 ml) was added and the mixture was extracted with ethyl acetate (4×25 ml). The combined organic extracts were washed with saturated sodium chloride solution (10 ml), dried (MgSO$_4$) and the solvent was removed by evaporation. The resultant oil was purified by MPLC, eluting with methanol/dichloromethane (1:12 v/v) to give methyl 4(Z)-erythro-8-hydroxy-7-hydroxymethyl-8-(3-pyridyl)-4-octenoate (C) as an oil (1.044 g); NMR (250 MHz, CDCl$_3$): 1.82(2H,m), 2.16(1H,m), 2.44(4H,m), 4.91(2H,b), 3.67(3H,s), 3.81(2H,d, J=3 Hz), 5.20(1H,d, J=2 Hz), 5.30(2H,m), 7.33(1H,m), 7.79(1H,m), 8.51(1H,m), 8.61(1H,m).

(iii) A solution of methanesulphonyl chloride (0.32 ml) in dichloromethane (2.0 ml) was added during ten minutes to a stirred solution of C (995 mg) and triethylamine (0.59 ml) in dichloromethane (20 ml). The mixture was stirred for a further 1 hour and then diluted with ethyl acetate (50 ml). The subsequent mixture was washed with water (2×15 ml), saturated sodium chloride solution (15. ml), and dried (MgSO$_4$). The solvent was removed by evaporation to give an oil which was purified by MPLC, eluting with methanol/dichloromethane (1:32 v/v), to give methyl 4(Z)-erythro-8-hydroxy-7-(methylsulphonyloxymethyl)-8-(3-pyridyl)-4-octenoate (D) as a colourless oil (886 mg); NMR (250 MHz, CDCl$_3$): 2.24(8H, m), 3.01(3H,s), 3.68(3H,s), 4.10(1H,m), 4.31(1H,m), 5.02(1H,d, J=2H), 5.38(2H,m), 7.34(1H,m), 7.77(1H,d, J=7 Hz), 8.57(2H,m).

(iv) Anhydrous potassium carbonate (994 mg) and trifluoroacetaldehyde hydrate (1.13 g) were added to a solution of D (857 mg) in dry THF (10 ml). The mixture was stirred for 15 minutes at ambient temperature and then at 60° C. for 5 hours. The mixture was then diluted with ethyl acetate (75 ml) and washed with water (25 ml), followed by saturated sodium chloride solution (25 ml). The organic phase was dried (MgSO$_4$) and the solvent was removed by evaporation. The resultant oil was purified by MPLC, eluting with ethyl acetate/hexane (7:3 v/v) to give, firstly, methyl 4(Z)-6-[2,4-trans, 4,5-cis)-4-(3-pyridyl)-2-trifluoromethyl-1,3-dioxan-5-yl]hexenoate as a colourless oil (137 mg); NMR (250 MHz, CDCl$_3$): 1.66 (1H,m), 2.02(1H,m), 2.29(4H,m), 2.43(1H,m), 3.66(3H,s), 3.96(1H,dd, J=11 and 2 Hz), 4.36(1H,dm, J=11 Hz), 5.20(1H,m), 5.30(1H,q, J=6 Hz), 5.42(1H,m), 5.48(1H,d, J=2 Hz), 7.35(1H,m), 7.71(1H,m), 8.59(2H,m), and then, methyl 4(Z)-6-[(2,4,5-cis)-4-(3-pyridyl)-2-trifluoromethyl-1,3-dioxan-5-yl]hexenoate (A) as a colourless oil (578 mg); NMR (250 MHz, CDCl$_3$): 1.60(1H,m), 1.81(1H,m), 2.30(4H,m), 2.55(1H,m), 3.66(3H,s), 4.04(1H,dm,J=11 Hz), 4.29(1H,d,J=11 Hz), 5.12(1H,q, J=3 Hz), 5.19(1H,d, J=2 Hz), 5.22(1H,m), 5.45(1H,m), 7.38(1H,m), 7.74(1H,m), 8.58(2H,m).

EXAMPLES 35–39

Using an analogous procedure to that described in Example 5, but replacing 3-pyridinecarboxaldehyde by the appropriate aldehyde of the formula R$^4$.CHO, the following acids of the formula III (A$^3$=ethylene) were obtained.

| Example | R$^4$ | $^1$H NMR (ppm) |
|---|---|---|
| 35 | 3NO$_2$–PhO.C(CH$_3$)$_2$– | 1.45(3H, s), 1.47(3H, s), 1.55–1.8(2H, m), 2.2–2.55(5H, m), 3.95–4.3(2H, m), 4.8(1H, s), 5.1–5.55(3H, m), 7.3–8.0(6H, m), 8.5–8.6(2H, m). |
| 36 | 2NO$_2$—PhO.C(CH$_3$)$_2$— | 1.45(6H, s), 1.5–1.8(2H, m), 2.15–2.5(5H, m), 3.9–4.2(2H, m), 4.85(1H, s), 5.1–5.5(3H, m), 7.1–7.8(6H, m), 8.4–8.6(2H, m). |
| 37 | 2,4-Cl$_2$—PhO.C(CH$_3$)$_2$— | 1.46(3H, s), 1.48(3H, s), 1.55–1.8(2H, m), 2.15–2.55(5H, m), 3.95–4.25(2H, m), 4.95(1H, s), 5.1–5.55(3H, m), 7.1–7.65(5H, m), 8.45–8.65(2H, m). |
| 38 | 4NO$_2$—PhCH$_2$C(CH$_3$)$_2$— | 1.0(3H, s), 1.02(3H, s), 1.5–1.75(2H, m), 2.25–2.6(5H, m), 2.85(2H, s), 3.8–4.2(2H, m), 4.3 (1H, s), 5.0–5.55(3H, m), 7.25–8.1(6H, m), 8.5–8.65(2H, m). |
| 39 | 3NO$_2$—PhCH$_2$C(CH$_3$)$_2$— | 1.02(3H, s), 1.04(3H, s), 1.5–1.75(2H, m), 2.25–2.6(5H, m), 2.85(2H, s), 3.85–4.25(2H, m), 4.3(1H, s), 5.0–5.55(3H, m), 7.35–8.1(6H, m), 8.5–8.65(2H, m). |

Using an analogous procedure to that described for the preparation of 2-methyl-2-(3-pyridyloxy)propionaldehyde, but starting from the appropriately substituted phenol, the following aldehydes used in Examples 35, 36 and 37 were obtained:

2-(3-nitrophenoxy)-2-methylpropanal; NMR: 1.5(6H,s), 7.15–7.95(4H,m), 9.85(1H,s):

2-(2-nitrophenoxy)-2-methylpropanal; NMR: 1.5(6H,s), 6.9–7.8(4H,m), 9.85(1H,s);

2-(2,4-dichlorophenoxy)-2-methylpropanal; NMR: 1.45(6H,s), 6.8–7.4(3H,m), 9.85(1H,s).

Using an analogous procedure to that described by R Subramanian, Chem. and Ind., 1978, page 731, for the preparation of 2,2-dimethyl-3-phenylpropanal, but starting from the appropriately substituted benzyl halide, the following aldehydes used in Examples 38 and 39 were obtained:

3-(4-nitrophenyl)-2,2-dimethylpropanal NMR: 1.1(6H,s), 2.9(2H,s), 7.3(2H,d,J=8 Hz), 8.15(2H,d,J=8 Hz), 9.55(1H,s);

3-(3-nitrophenyl)-2,2-dimethylpropanal; NMR: 1.1(6H,s), 2.9(2H,s), 7.45–8.15(4H,m), 9.6(1H,s).

EXAMPLE 40

Using an analogous procedure to that described in Example 5, but starting from 4(Z)-6-[(4S,5R)-2,2-dimethyl-4-(3-pyridyl)-1,3-dioxan-5-yl]hexenoic acid and 2-(4-bromophenoxy)-2-methylpropanal, there was obtained 4(Z)-6-[(2S,4S,5R)-2-[1-(4-bromophenoxy)-1-methylethyl]-4-(3-pyridyl)-1,3-dioxan-5-yl]hexenoic acid as an oil with $^{25}[\alpha]_D$ −98.5° (EtOH, c 0.48) and NMR essentially identical with that of the racemic material described in Example 11.

The starting 2,2-dimethyl-1,3-dioxane derivative was obtained as follows:

(i) A 1.53M solution of butyllithium in hexane (23.9 ml) was added to a solution of 4S-(−)-isopropyl-2-oxazolidinone (4.68 g) in dry THF (75 ml), cooled to −78° C. under argon. The mixture was allowed to warm to −50° C. and then stirred for 30 minutes. The mixture was then recooled to −78° C. and a solution of 4-pentenoyl chloride (4.33 g) in dry THF (10 ml) was added dropwise. After the addition, the mixture was stirred at −78° C. for 30 minutes, and then allowed to warm to −20° C. Saturated aqueous ammonium chloride solution (20 ml) was added and the mixture was extracted with ethyl acetate (3×100 ml). The combined organic phases were dried (MgSO$_4$) and concentrated. The residue was purified by flash column chromatography, eluting with ethyl acetate/- hexane (20:80 v/v) to give (4S)-4-isopropyl-3-(4-pentenoyl)oxazolidin-2-one (A) (6.34 g), as an oil; NMR: 0.85–0.95(6H,m), 2.3–2.5(3H,m), 2.9–3.2(2H,m), 4.15–4.5(3H,m), 4.95–5.15(2H,m), 5.75–6.0(1H,m).

(ii) A 1M solution of dibutylboron triflate in dichloromethane (32.7 ml) was added to a solution of A (6.28 g) in dry dichloromethane (110 ml), cooled to 5° C. under argon, followed by diisopropylethylamine (6.25 ml). The reaction mixture was stirred at 5° C. for 30 minutes and then cooled to -78° C. 3-Pyridinecarboxaldehyde (3.1 ml) was added dropwise. The mixture was stirred for 30 minutes at −78° C. and then allowed to warm to −50° C. over 30 minutes. The cooling bath was removed and the reaction mixture was stirred at room temperature for 2 hours. The mixture was then cooled to 5° C. and hydrogen peroxide (11.5 ml, 30% w/v aqueous solution) was added. The mixture was stirred for 30 minutes and then poured into water (50 ml) and extracted with dichloromethane (3×100 ml). The combined extracts were dried (MgSO$_4$) and evaporated. The residue was purified by flash column chromatography, eluting with ethyl acetate/hexane (1:1 v/v, gradually increasing to 100% ethyl acetate),to give (4S)-(3-[(2S)-2-[(1S-1-hydroxy-1-(3-pyridyl)methyl]pent-4-enoyl)-4-isopropyloxazolidin-2-one (B), as a solid, m.p. 112°–113° C. (after recrystallisation from toluene); $^{25}[\alpha]_D = +136.0$ (EtOH, c 0.311); NMR: 0.85(6H,dd,J=7 Hz), 2.15–2.7(4H,m), 4.0–4.2(2H,m), 4.3–4.55(2H,m 4.95–5.1(3H,m), 5.65–5.9(1H,m), 7.25–7.35(1H,m), 7.75–7.85(1H,m), 8.5–8.65(2H,m).

(iii) A 30 wt. % solution of sodium methoxide in methanol (3.65 ml) was added to a solution of B (5.76 g) in methanol (40 ml), cooled to 5° C. The mixture was stirred for 15 minutes and then saturated aqueous ammonium chloride solution (10 ml) and ether (50 ml) were added. Sufficient water was added to dissolve any precipitated inorganics and the mixture was then extracted with ether (3×50 ml). The combined extracts were dried (MgSO$_4$) and evaporated. The residue was purified by flash column chromatography, eluting with ethyl acetate to give methyl (2S)-2-[(1S)-1-hydroxy-1-(3-pyridyl)methyl]pent-4-enoate (C) (3.245 g) as an oil; NMR: 2.3–2.6(2H,m), 2.8–2.9(1H,m), 3.6(3H,s), 4.95–5.1(3H,m), 5.65–5.85(1H,m), 7.25–7.35(1H,m), 7.7–7.75(1H,m), 8.45–8.6(2H,m).

(iv) A solution of C (3.88 g) in THF (10 ml) was added dropwise to a cooled suspension of lithium aluminium hydride (767 mg) in THF (50 ml) at such a rate to maintain the temperature below 10° C. After the addition was complete, the mixture was stirred at 5° C. for 4 hours. Ethyl acetate (20 ml) was added, followed by saturated aqueous ammonium chloride solution (10 ml) and water (10 ml). The mixture was extracted with ethyl acetate (3×50 ml). The combined extracts were dried (MgSO$_4$) and evaporated. The residue was purified by flash column chromatography, eluting with ethyl acetate, gradually increasing to methanol/ethyl acetate (1:9 v/v), to give (1S,2R)-2-allyl-1-(3-pyridyl)-1,3-propanediol (D) (2.69 g) as an oil; NMR: 1.65–1.8(1H,m), 1.95–2.15(2H,m), 3.15–3.45(2H,m), 4.4–4.5(1H,m), 4.75–5.0(3H,m), 5.25(1H,d,J=7 Hz), 5.6–5.85(1H,m), 7.3–7.4(1H,m), 7.65–7.7(1H,m), 8.4–8.5(2H,m).

(v) p-Toluenesulphonic acid monohydrate (2.91 g) was added to a solution of D (2.68 g) in 2,2-dimethoxypropane (15 ml) and the mixture was stirred for 18 hours. Triethylamine (10 ml) was added and the mixture was partitioned between ether (50 ml) and water (20 ml). The organic layer was dried (MgSO$_4$) and evaporated. The residue was purified by flash column chromatography, eluting with ethyl acetate/hexane (1:1 v/v) to give (4S,5R)-5-allyl-2,2-dimethyl-4-(3-pyridyl)-1,3-dioxane (E) (2.39 g), as an oil; NMR: 1.53(3H,s), 1.55(3H,s), 1.6–1.75(1H,m), 1.9–2.0(1H,m), 2.3–2.5(1H,m), 3.85–4.2(2H,m), 4.9–5.0(2H,m), 5.27(1H,d,J=3 Hz), 5.45–5.7(1H,m), 7.25–7.35(1H,m), 7.65–7.7(1H,m), (8.5–8.6(2H,m).

(vi) Ozone was passed through a solution of the allyl compound (E) (530 mg) in methanol (30 ml) cooled to −78° C., until a blue colouration was formed. The mixture was purged with argon before methyl sulphide (1.6 ml) was added. The mixture was then stirred at room temperature for 18 hours, before being concentrated in vacuo and partitioned between ether (50 ml) and water (20 ml). The organic layer was dried (MgSO$_4$) and evaporated. The residue was purified by flash column chromatography, eluting with a mixture of methanol and methylene chloride (5:95 v/v) to give 2-[4S,5R)-2,2-dimethyl-4-(3-pyridyl)-1,3-dioxan-5-yl]acetaldehyde (F), as an oil; NMR: 1.53(3H,s), 1.55(3H,s), 2.15–2.4(2H,m), 2.85–2.95(1H,m), 3.8–3.85(1H,m), 4.25–4.35(1H,m), 5.28(1H,d,J=3 Hz), 7.25–7.7(2H,m), 8.5–8.6(2H,m), 9.6(1H,s).

[Note: The optical purity was assessed as >99% by proton NMR by addition of (R)-(−)-2,2,2-trifluoro-1-(9-anthryl)ethanol and observing the region 2.7–2.9 (delta), which showed 4 doublets centred at 2.77, 2.71, 2.82 and 2.85 (1H,.CH—CHO)].

(vii) The acetaldehyde (F) is then converted to 4(Z)-6-[(4S,5R)-2,2-dimethyl-4-(3-pyridyl)-1,3-dioxan-5-yl]hexenoic acid, having $^{25}[\alpha]_D - 113.3$ (EtOH, c 0.465) and NMR essentially identical with that of the racemic material described in Example 1, using an analogous procedure to that described in the first part of Example 1.

EXAMPLE 41

Illustrative pharmaceutical dosage forms include the following tablet, capsule, injection and aerosol formulations, which may be obtained by conventional procedures well known in the art of pharmacy and are suitable for therapeutic or prophylactic use in humans:

|  | mg/tablet |
|---|---|
| (a) Tablet I | |
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |
| (b) Tablet II | |
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| (c) Tablet III | |
| Compound Z* | 100 |
| Lactose Ph. Eur. | 182.75 |
| Croscarmellose sodium | 12.0 |
| Maize starch paste (5% W/V aqueous paste) | 2.25 |
| Magnesium stearate | 3.0 |

|  | mg/capsule |
|---|---|

|  |  |
|---|---|
| (d) Capsule | |
| Compound Z* | 10 mg |
| Lactose Ph. Eur. | 488.5 |
| Magnesium stearate | 1.5 |
| (e) Injection I (50 mg/ml) | |
| Compound Z* (free acid form) | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |
| (f) Injection II (10 mg/ml) | |
| Compound Z* (free acid form) | 1.0% w/v |
| Sodium phosphate EP | 3.6% w/v |
| 0.1M Sodium hydroxide solution | 15.0% v/v |
| Water for injection to 100% | |
| (g) Injection III (1 mg/ml, buffered to pH 6) | |
| Compound Z* (free acid form) | 0.1% w/v |
| Sodium phosphate BP | 2.26% w/v |
| Citric acid | 0.38% w/v |
| Polyethylene glycol 400 | 3.5% w/v |
| Water for injection to 100% | |

|  | mg/ml |
|---|---|
| (h) Aerosol I | |
| Compound Z* | 10.0 |
| Sorbitan trioleate | 13.5 |
| Trichlorofluoromethane | 910.0 |
| Dichlorodifluoromethane | 490.0 |
| (i) Aerosol II | |
| Compound Z* | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | |
| Compound Z* | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | |
| Compound Z* | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note
*Compound Z is a compound of formula I, or a salt thereof, for example a compound of formula I described in any preceding Examples, and especially as described in Example 4, 8, 11 or 28.

The tablet compositions (a)–(c) may be enteric coated by conventional means, for example to provide a coating of cellulose acetate phthalate. The aerosol compositions (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

SCHEME 1

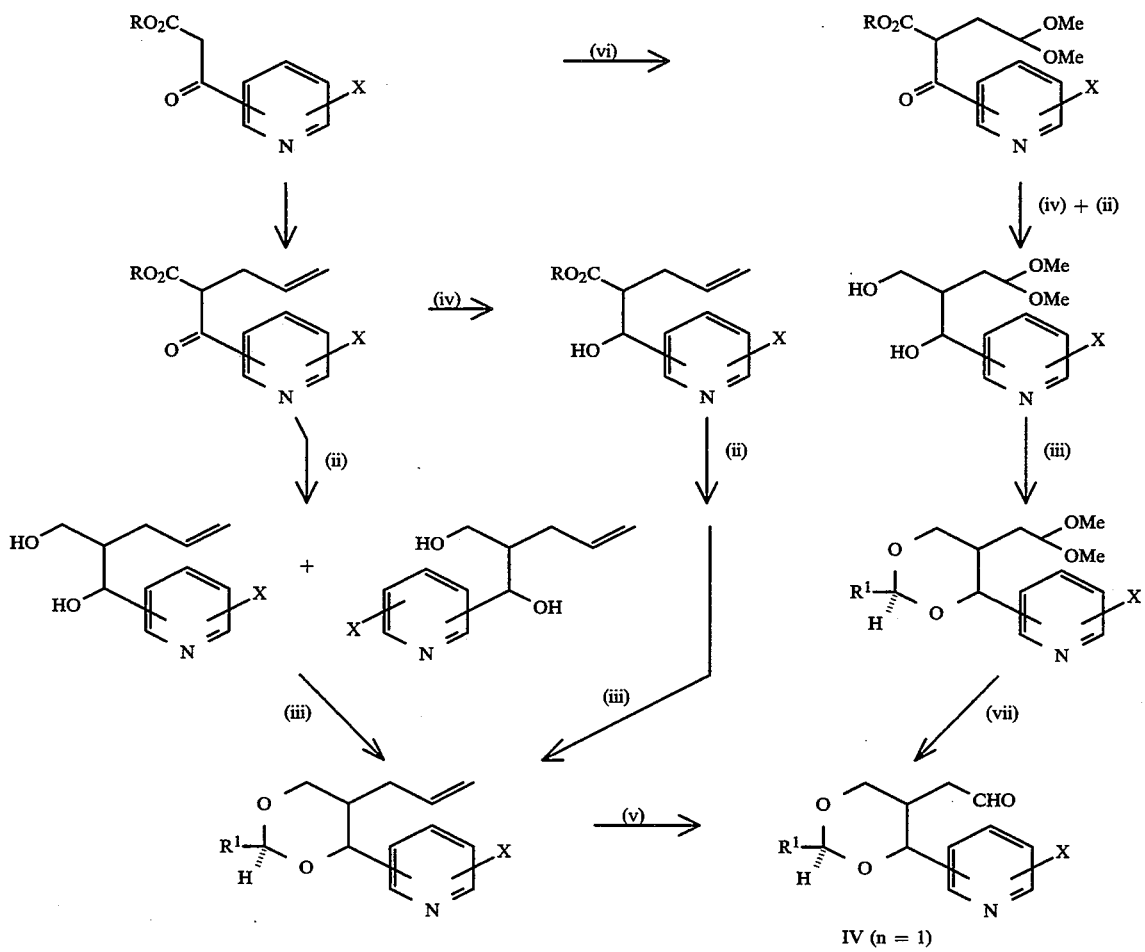

-continued
SCHEME 1

Reagents:

(i) NaOEt/EtOH/allyl bromide
(ii) LiAlH$_4$ or LiBH$_4$/THF
(iii) p-Ts.OH/R$^1$.CHO or R$^1$.C(OMe)$_2$
(iv) Zn(BH$_4$)$_2$/Et$_2$O
(v) O$_3$/CH$_2$Cl$_2$, then Me$_2$S or Ph$_3$P
(vi) NaH/DMSO/BrCH$_2$CH(OMe)$_2$
(vii) H$^+$/H$_2$O

[R = (1-4C)alkyl such as Me]

SCHEME 2

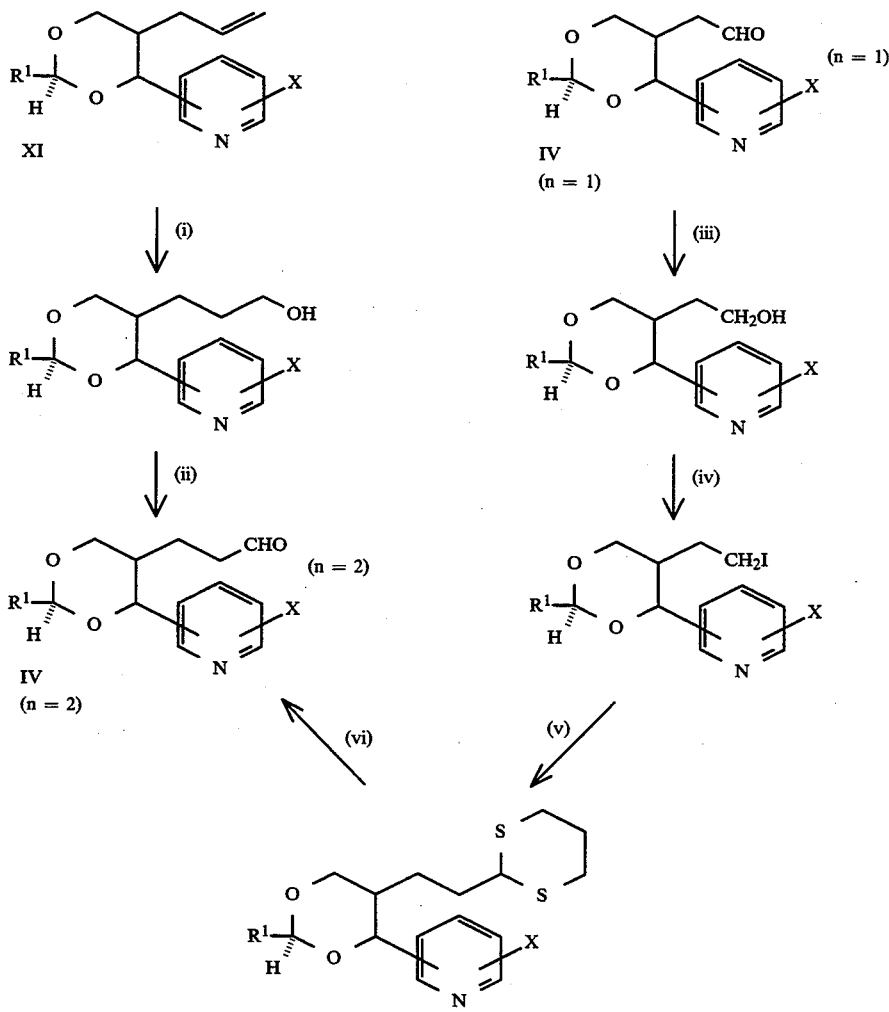

Reagents:

(i) B$_2$H$_6$; then H$_2$O$_2$
(ii) pyridinium chlorochromate/CH$_2$Cl$_2$; or DCCI/DMSO/pyridine/TFA
(iii) NaBH$_4$/EtOH
(iv) p-TsCl/pyridine; NaI/Me$_2$CO, heat
(v) (i-Pr)$_2$NLi/1,3-dithiane/−78° C.
(vi) (NH$_4$)$_2$Ce(NO$_3$)$_6$, 0° C.

SCHEME 3

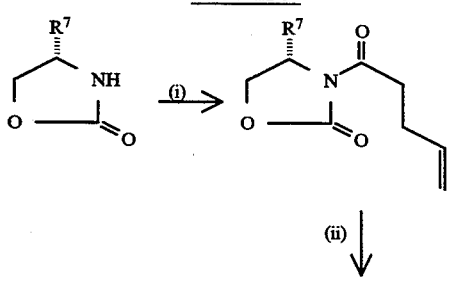

SCHEME 3
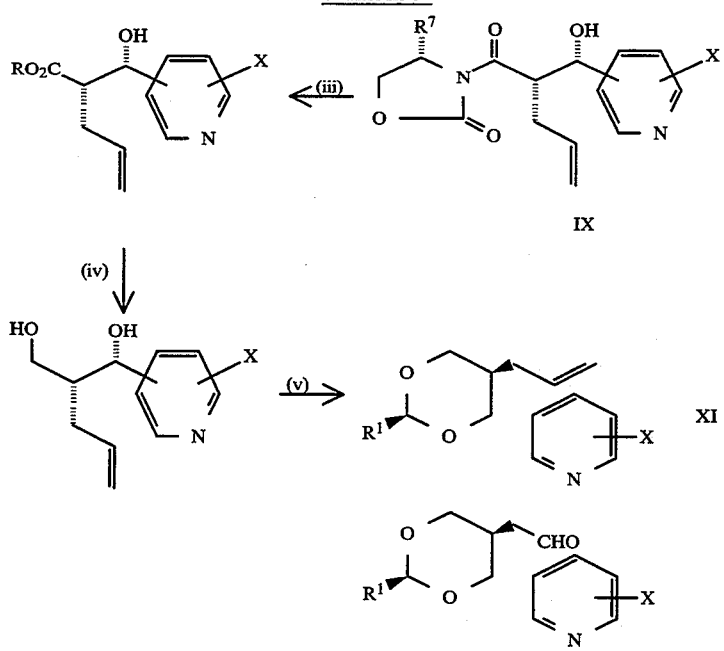
Reagents:
(i) pentenoyl chloride/BuLi/THF/−78° C.
(ii) Bu$_2$B.SO$_2$CF$_3$/(i-Pr)$_2$NH.Et/pyridinecarboxaldehyde/CH$_2$Cl$_2$; H$_2$O$_2$/pH7
(iii) NaOR/ROH [R = (1–4C)alkyl such as Me]
(iv) LiAlH$_4$/THF
(v) R$^1$.CHO/p-toluenesulphonic acid (p-Ts.OH)
(vi) O$_3$/CH$_2$Cl$_2$, then Me$_2$S or Ph$_3$P
CHEMICAL FORMULAE
(Description)
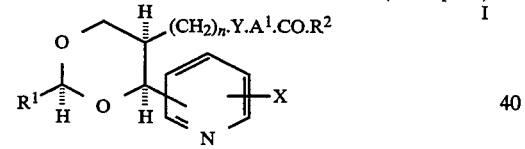 I
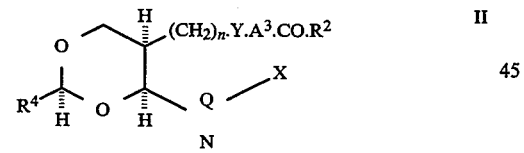 II
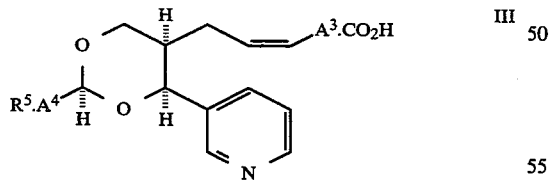 III
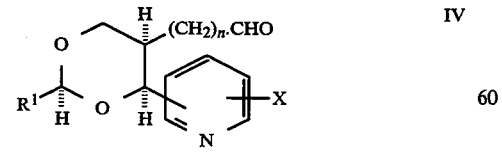 IV
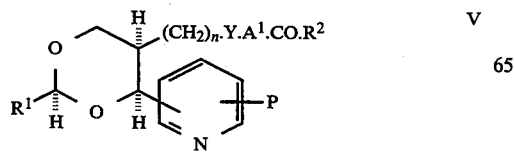 V
-continued
CHEMICAL FORMULAE
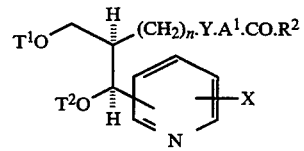 VI
VII
VIII
IX

CHEMICAL FORMULAE

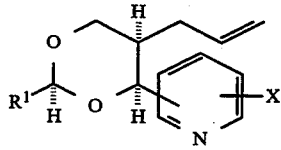
XI

What is claimed includes:

1. A 2,2-disubstituted 1,3-dioxane of the formula VII

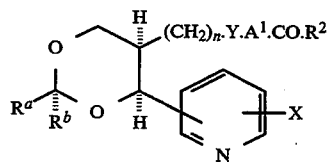
VII wherein one of Ra and Rb is methyl or ethyl and the other is methyl or ethyl, and
wherein
$A^1$ is (1–6C)alkylene;
$R^2$ is hydroxy, a physiologically acceptable alcohol residue, or (1–4C)alkanesulphonamido;
X is hydrogen, hydroxy or (1–4C)alkoxy;
Y is vinylene; and
n is the integer 1 or 2; or a pharmaceutically acceptable salt thereof.

2. A 2,2-disubstituted 1,3-dioxane of the formula VII as claimed in claim 1 selected from the group consisting of 4(Z)-6-[2,2-dimethyl-4-(3-pyridyl)-1,3-dioxan-cis-5-yl]hexenoic acid and 4(Z)-6-[(4S,5R)-2,2-dimethyl-4-(3-pyridyl)-1,3-dioxan-5-yl]hexenoic acid.

3. A 4-pyridyl-5-allyl-1,3-dioxane of the formula XI

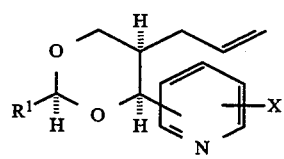
XI wherein:
$R^1$ is (1–6C)alkyl, trifluoromethyl, (3–6C)cycloalkyl or (1–4C)alkoxy(1–4C)alkyl, or is a group of the formula $R^3.A^2$- in which $R^3$ is pyridyl, phenyl or phenyl bearing 1 or 2 substituents selected from halogeno, trifluoromethyl, nitro and cyano, and in which $A^2$ is (1–6C)alkylene, oxy(1–6C)alkylene, (2–6C)alkenylene or a direct bond to $R^3$; and
X is hydrogen, hydroxy or (1–4C)alkoxy.

* * * * *